US011089994B2

(12) United States Patent
Goldstein

(10) Patent No.: US 11,089,994 B2
(45) Date of Patent: Aug. 17, 2021

(54) DEVICE TO DETECT AND TREAT APNEAS AND HYPOPNEA

(71) Applicant: WhisperSom Corporation, Annapolis, MD (US)

(72) Inventor: David Brian Goldstein, Groton, MA (US)

(73) Assignee: WhisperSom Corporation, Annapolis, MD (US)

( * ) Notice: Subject to any disclaimer, the term of this patent is extended or adjusted under 35 U.S.C. 154(b) by 0 days.

(21) Appl. No.: 15/963,709

(22) Filed: Apr. 26, 2018

(65) Prior Publication Data
US 2018/0289316 A1 Oct. 11, 2018

Related U.S. Application Data

(63) Continuation of application No. 12/277,386, filed on Nov. 25, 2008, now abandoned.
(Continued)

(51) Int. Cl.
A61B 5/00 (2006.01)
A61B 7/00 (2006.01)
(Continued)

(52) U.S. Cl.
CPC .......... A61B 5/4818 (2013.01); A61B 5/0205 (2013.01); A61B 5/085 (2013.01);
(Continued)

(58) Field of Classification Search
CPC ... A61B 5/7405; A61B 5/4818; A61B 5/0205; A61B 5/0806; A61B 5/085; A61B 5/486;
(Continued)

(56) References Cited

U.S. PATENT DOCUMENTS 2,107,855 A * 2/1938 Drexler .................. B62B 9/102
5/210
4,296,757 A 10/1981 Taylor
(Continued)

FOREIGN PATENT DOCUMENTS

EP 1308181 A2 * 5/2003 ........... A61N 1/3601
EP 1308181 11/2007
(Continued)

OTHER PUBLICATIONS

U.S. Appl. No. 14/535,561, 2015-0173672, filed Jun. 25, 2015.
(Continued)

Primary Examiner — Lynsey C Eiseman
Assistant Examiner — Amanda L Steinberg
(74) Attorney, Agent, or Firm — DLA Piper LLP (US)

(57) ABSTRACT

A method and apparatus for the treatment of Sleep Apnea events and Hypopnea episodes wherein one embodiment comprises a wearable, belt like apparatus containing a microphone and a plethysmograph. The microphone and plethysmograph generate signals that are representative of physiological aspects of respiration, and the signals are transferred to an imbedded computer. The embedded computer extracts the sound of breathing and the sound of the heart beat by Digital Signal Processing techniques. The embedded computer has elements for determining when respiration parameters falls out of defined boundaries for said respiration parameters. This exemplary method provides real-time detection of the onset of a Sleep Apnea event or Hypopnea episode and supplies stimulation signals upon the determination of a Sleep Apnea event or Hypopnea episode to initiate an inhalation. In one embodiment, the stimulus is applied to the patient by a cutaneous rumble effects actuator and/or audio effects broadcasting.

34 Claims, 8 Drawing Sheets

Related U.S. Application Data

(60) Provisional application No. 60/990,035, filed on Nov. 26, 2007.

(51) Int. Cl.
  *A61B 5/08* (2006.01)
  *A61B 5/085* (2006.01)
  *A61B 5/0205* (2006.01)

(52) U.S. Cl.
  CPC ............ *A61B 5/0806* (2013.01); *A61B 5/486* (2013.01); *A61B 5/6817* (2013.01); *A61B 5/6831* (2013.01); *A61B 5/7264* (2013.01); *A61B 5/7282* (2013.01); *A61B 5/741* (2013.01); *A61B 5/7455* (2013.01); *A61B 7/003* (2013.01); *A61B 5/7405* (2013.01)

(58) Field of Classification Search
  CPC ... A61B 5/6817; A61B 5/6831; A61B 5/7264; A61B 5/7282; A61B 5/741; A61B 5/7455; A61B 7/003
  See application file for complete search history.

(56) References Cited

U.S. PATENT DOCUMENTS

| | | |
|---|---|---|
| 4,365,636 A | 12/1982 | Barker |
| 4,655,213 A | 4/1987 | Rapoport et al. |
| 4,773,411 A | 9/1988 | Downs |
| 4,781,201 A | 11/1988 | Wright et al. |
| 5,050,614 A | 9/1991 | Logan |
| 5,107,855 A | 4/1992 | Harrington et al. |
| 5,277,194 A | 1/1994 | Hosterman et al. |
| 5,295,490 A | 3/1994 | Dodakian |
| 5,522,862 A | 6/1996 | Testerman et al. |
| 5,540,733 A | 7/1996 | Testerman et al. |
| 5,555,891 A | 9/1996 | Eisenfeld |
| 5,671,733 A | 9/1997 | Raviv |
| 5,686,999 A | 11/1997 | Mizuno et al. |
| 5,694,839 A | 12/1997 | Wohl et al. |
| 5,769,084 A | 6/1998 | Katz et al. |
| 5,853,005 A * | 12/1998 | Scanlon ............... A61B 5/113 600/459 |
| 6,011,477 A | 1/2000 | Teodorescu et al. |
| 6,236,622 B1 | 5/2001 | Blackman |
| 6,241,683 B1 | 6/2001 | Macklem et al. |
| 6,290,654 B1 | 9/2001 | Karakasoglu |
| 6,484,719 B1 | 11/2002 | Berthon-Jones |
| 6,539,940 B2 | 4/2003 | Zdrojkowski et al. |
| 6,666,830 B1 | 12/2003 | Lehrman et al. |
| 6,935,335 B1 * | 8/2005 | Lehrman .............. A61B 5/0002 128/200.24 |
| 7,225,021 B1 | 5/2007 | Park |
| 7,225,064 B2 | 5/2007 | Fudali et al. |
| 7,371,220 B1 | 5/2008 | Koh et al. |
| 7,387,608 B2 | 6/2008 | Dunlop et al. |
| 7,426,435 B2 | 9/2008 | Gauthier et al. |
| 7,734,350 B2 | 6/2010 | Dubnov et al. |
| 7,748,493 B2 | 7/2010 | Moses et al. |
| 7,749,155 B1 * | 7/2010 | Anderson ............. A61M 21/00 600/26 |
| 8,630,712 B2 | 1/2014 | Moses et al. |
| 8,834,347 B2 | 9/2014 | Henke et al. |
| 2004/0056840 A1 | 3/2004 | Goldenberg |
| 2004/0073098 A1 | 4/2004 | Geva et al. |
| 2004/0230105 A1 | 11/2004 | Geva et al. |
| 2005/0085865 A1 | 4/2005 | Tehrani |
| 2005/0101833 A1 | 5/2005 | Hsu et al. |
| 2005/0197588 A1 | 9/2005 | Freeberg |
| 2005/0217674 A1 | 10/2005 | Burton et al. |
| 2006/0097879 A1 | 5/2006 | Lippincott |
| 2007/0213785 A1 | 9/2007 | Osorio et al. |
| 2008/0009915 A1 | 1/2008 | Moses et al. |
| 2008/0103545 A1 | 5/2008 | Bolea et al. |
| 2008/0183239 A1 | 7/2008 | Tehrani et al. |
| 2008/0200774 A1 | 8/2008 | Luo |
| 2008/0214903 A1 | 9/2008 | Orbach |
| 2008/0264426 A1 | 10/2008 | Walker |
| 2009/0020121 A1 | 1/2009 | Bassin |
| 2009/0054737 A1 | 2/2009 | Magar et al. |
| 2009/0076405 A1 | 3/2009 | Amurthur et al. |
| 2009/0082639 A1 | 3/2009 | Pittman et al. |
| 2009/0240119 A1 | 9/2009 | Schwaibold et al. |
| 2009/0287265 A1 | 11/2009 | Henke |
| 2010/0048986 A1 | 2/2010 | Henke et al. |
| 2010/0056852 A1 | 3/2010 | Henke et al. |
| 2010/0056855 A1 | 3/2010 | Henke et al. |
| 2010/0056879 A1 | 3/2010 | Greenspan et al. |
| 2010/0057148 A1 | 3/2010 | Henke et al. |
| 2010/0063348 A1 | 3/2010 | Henke et al. |
| 2010/0063350 A1 | 3/2010 | Henke et al. |
| 2010/0076251 A1 | 3/2010 | Stasz et al. |
| 2010/0076252 A1 | 3/2010 | Henke |
| 2011/0040713 A1 | 2/2011 | Colman et al. |
| 2012/0184825 A1 | 7/2012 | Ben David |
| 2012/0310050 A1 | 12/2012 | Osorio |
| 2014/0051938 A1 | 2/2014 | Goldstein et al. |
| 2014/0275850 A1 | 9/2014 | Venkatraman et al. |
| 2014/0277255 A1 | 9/2014 | Sabesan |
| 2015/0065832 A1 | 3/2015 | Manion |
| 2016/0045154 A1 | 2/2016 | Addison et al. |
| 2016/0056840 A1 | 2/2016 | Siegert et al. |
| 2017/0368329 A1 * | 12/2017 | Tyler .................. A61N 1/36036 |

FOREIGN PATENT DOCUMENTS

| | | | |
|---|---|---|---|
| WO | WO1996028093 A1 * | 9/1996 | ............ A61B 5/113 |
| WO | WO 2004032719 A2 * | 4/2004 | ............ A61B 5/04 |
| WO | WO2009/036327 | 3/2009 | |
| WO | WO2014/165834 | 10/2014 | |

OTHER PUBLICATIONS

H. Attias et al., "Coding of Natural Stimuli by Auditory Midbrain Neurons", Advances in Neural information Processing Systems, vol. 10, pp. 103-109 (1998).

Brian D. Wright et al, "Spike Timing and the Coding of Naturalistic Sounds in a Central Auditory Area of Songbirds," 15th Annual Neural Infomration Processing Systems Conference, NIPS 2001—Vancouver, BC, Canada, Dec. 3-8, 2001, published Jan. 1, 2002, (8 pages).

Adriana Bruscato et al., "Spectral Anslysis of Non-Stationary Processes using the Fourier Transform," Brazilian Journal of Probabilty and Statistics, vol. 18, pp. 69-102 (2004).

Adrien Meynard et al., "Spectral Analysis for Nonstationary Audio," arXiv:1712.10252v3 [eess.AS] Aug. 23, 2018 (26 pages).

Michelle Moerel et al., "Processing of Natural Sounds in Human Auditory Cortex: Tonotopy, Spectral Tuning, and Relation to Voice Sensitivity," The Journal of Neuroscience, vol. 32, No. 41, pp. 14205-14216, Oct. 10, 2012.

F. Rieke, et al., "Naturalistic Stimuli Increase the Rate and Efficiency of Information Transmission by Primary Auditory Afferents," Proc. R. Soc. Lond. B, vol. 262, pp. 259-265 (1995).

"Non-Stationary Nature of Speech Signal," Downloaded from vlab.amrita.edu/?sub=3brch=164&sim=371&cnt=1104 on Dec. 6, 2019 (6 pages).

Maria Sandsten, "Time-Frequency Analysis of Time-Varying Signals and Non-Stationary Processes," Lund University, Centre for Mathematical Sciences (2018) (95 pages).

Amy S. Jordan et al., "Termination of Respiratory Events with and without Cortical Arousal in Obstructive Sleep Apnea", American Journal of Respiratory and Critical Care Medicine, vol. 184, pp. 1183-1191 (2011).

Magdy Younes, "Role of Respiratory Control Mechanisms in the Pathogenesis of Obstructive Sleep Disorders", J. Appl. Physiol., vol. 105, pp. 1389-1405, Sep. 11, 2008.

Wataru Hida et al., "Effects of Submental Stimulation for Several Consecutive Nights in Patients with Obstructive Sleep Apnoea", Thorax, vol. 49, pp. 446-452 (1994).

(56) References Cited

OTHER PUBLICATIONS

Christian Guilleminault et al., "The Effect of CNS Activation Versus EEG Arousal During Sleep on Heart Rate Response and Daytime Tests", Clinical Neurophysiology, vol. 117, pp. 731-739 (2006).
Robert C. Basner et al., "Effect of Induced Transient Arousal on Obstructive Apnea Duration", J. Appl. Physiol. vol. 78, No. 4, pp. 1469-1476 (1995).
Abstract of D.M. Carlson et al., "Acoustically Induced Cortical Arousal increases Phasic Pharyngeal Muscle and Diaphragmatic EMG in NREM Sleep", Journal of Applied Physiology, vol. 76, No. 4, pp. 1553-1559 (1994).
David W. Carley et al., "Respiratory and Arousal Responses to Acoustic Stimulation", Chest, vol. 112, No. 6, pp. 1567-1571, Dec. 1997.
Amy S. Jordan et al., "The Influence of Gender and Upper Airway Resistance on the Ventilatory Response to Arousal in Obstructive Sleep Apnoea in Humans", J. Physiol., vol. 558, No. 3, pp. 993-1004 (2004).
Riccardo Stoohs et al., "Cardiobascular Changes Associated with Obstructive Sleep Apnea Syndrome", J. Appl. Physiol. vol. 72, No. 2, pp. 583-589 (1992).
Amy S. Jordan et al., "Ventilatory Response to Brief Arousal from Non-Rapid Eye Movement Sleep is Greater in Men Than in Women", Am. J. Respir. Crit. Care Med., vol. 168, pp. 1512-1519 (2003).
Jose Haba-Rubio et al., "Obstructive Sleep Apnea Syndrome: Effect of Respiratory Events and Arousal on Pulse Wave Amplitude Measured by Photoplethysmography in NREM Sleep", Sleep Breath, vol. 9, pp. 73-81, May 4, 2005.
Akiko Noda et al., "Age Related Differences in Electroencephalographic and Cardiac Arousal at the Termination of Sleep Apnea/Hypopnea", Internal Medicine, vol. 39, pp. 375-380, May 2000.
John R. Stradling et al., "Variation in the Arousal Pattern After Obstructive Events in Obstructive Sleep Apnea", Am. J. Respir. Crti. Care Med., vol. 159, pp. 130-136 (1999).
Mary J. Morrell et al., "Progressive Retropalatal Narrowing Preceding Obstructive Apnea", Am. J. Respir. Crit. Care Med. vol. 15, pp. 1974-1981 (1998).
H. Schneider et al., "Inspiratory duty cycle responses to flow limitation predict nocturnal hypoventilation", Eur. Respir. J., vol. 33, No. 5, pp. 1068-1076 (2009).
Michelle Ball et al., "The salience of fire alarm signals for sleeping individuals: A novel approach to signal design", in Proceedings of the 13th International Symposium on Human Behaviour in Fire, Belfast, Northern Ireland, London: Interscience Communications, pp. 303-314, Sep. 2004.
Magdy Younes, "Role of Arousals in the Pathogenesis of Obstructive Sleep Apnea", Am. J. Respir. Crit. Care Med., vol. 169, pp. 623-633 (2004).
Homer Nazeran et al., "A Fuzzy Inference System for Detecting of Obstructive Sleep Apnea", Proceedings of the 23rd Annual Conference IEEE/EMBS, Oct. 25-28, 2001 (4 pages).
H. Schneider et al., "Effects of Arousal and Sleep State on Systemic and Pulmonary hemodynamics in Obstructive Apnea", J. Appl. Physiol., vol. 88, pp. 1084-1092 (2000).
W.T. McNicholas, "Arousal in the Sleep Apnea Syndrome: A Mixed Blessing?", Eur. Respir. J., vol. 12, pp. 1239-1241 (1998).
Dina Brooks et al., "Obstructive Sleep Apnea as a Cause of Systemic Hypertension: Evidence from a Canine Model", J. Clin. Invest., vol. 99, No. 1, pp. 106-109, Jan. 1997.
Mary J. Morrell et al., "Sleep Fragmentation, Awake Blood Pressure, and Sleep-Disordered Breathing in a Population-Based Study", Am. J. Respir. Crit. Care Med., vol. 162, pp. 2091-2096 (2000).
Richard S.T. Leung et al., "Sleep Apnea and Cardiovascular Disease", Am. J. Respir. Crit Care Med., vol. 164, pp. 2147-2165 (2001).
Denise M. O'Driscoll et al., "Cardiovascular Response to Arousal from Sleep Under Controlled Conditions of Central and Peripheral Chemoreceptor Stimulation in Humans", J. Appl. Physiol., vol. 96, pp. 865-870 (2004).

Denise M. O'Driscoll et al., "Occlusion of the Upper Airway Does Not Augment the Cardiovascular Response to Arousal from Sleep in Humans", J. Appl. Physiol., vol. 98, pp. 1349-1355 (2005).
Richard B. Berry et al., "Sleep Apnea Impairs the Arousal Response to Airway Occlusion", Chest, vol. 109, pp. 1490-1496 (1996).
T. Kato et al., "Experimentally Induced Arousals During Sleep: A Cross-Modality matching Paradigm", J. Sleep Res., vol. 13, pp. 229-238 (2004).
Emilia Sforza et al., "Effects of Sleep Deprivation on Spontaneous Arousals in Humans", Sleep, vol. 27, No. 6, pp. 1068-1075 (2004).
J.F. Masa et al., "Assessment of Thoracoabdominal Bands to Detect Respiratory Effort-Related Arousal", Eur. Respir. J., vol. 22, pp. 661-667 (2003).
Hiroshi Miki et al., "A New Treatment for Obstructive Apnea Syndrome by Electrical Stimulation of Submental Region", Tohoku J. Exp. Med., vol. 154, pp. 91-92 (1988).
Sheroz Khan et al., "Rule-Based Fuzzy Logic Controller with Adaptable Reference", Proceedings of World Academy of Science, Engineering and Technology, vol. 26, pp. 586-590, Dec. 2007.
E. Sforza et al., "Nocturnal Evolution of Respiratory Effort in Obstructive Sleep Apnoea Syndrome: Influence on Arousal Threshold", Eur. Respir. J., vol. 12, pp. 1257-1263 (1998).
Fatima H. Sert Kuniyoshi et al., "Day-Night Variation of Acute Myocardial Infarction in Obstructive Sleep Apnea", Journal of the American College of Cardiology, vol. 52, No. 5, pp. 343-346, Jul. 29, 2008.
Indu Ayappa et al., "Hypercapnia and Ventilatory Periodicity in Obstructive Sleep Apnea Syndrome", Am. J. Respir. Crit. Care Med., vol. 166, pp. 1112-1115 (2002).
Christian Guilleminault et al., "Arousal, Increased Respiratory Efforts, Blood Pressure and Obstructive Sleep Apnoea", J. Sleep Res., vol. 4, Suppl. 1, pp. 117-124 (1995).
Paolo Verdecchia et al., "Ambulatory Blood Pressure and Cardiovascular Outcome in Relation to Perceived Sleep Deprivation", Hypertension, vol. 49, pp. 777-783, Jan. 29, 2007.
In-Young Yoon et al., "Degree of Arousal in Most Correlated with Blood Pressure Reactivity During Sleep in Obstructive Sleep Apnea", J. Korean Med. Sci., vol. 16, pp. 707-711 (2001).
Yuksel Peker et al., "Respiratory Disturbances Index: An Independent Predictor of Mortality in Coronary Artery Disease", Am. J. Respir. Crit. Care Med., vol. 162, pp. 81-86 (2000).
Sarah-Jane C. Lusina et al., "Long-Term Intermittent Hypoxia Increases Sympathetic Activity and Chemosensitivity During Acute Hypoxia in Humans", J. Physiol., vol. 575, No. 3, pp. 961-970, Jun. 29, 2006.
Jerome A. Dempsey et al., "The Ventilatory Responsiveness to CO2 Below Eupnoea as a Determinant of Ventilatory Stability in Sleep", J. Physiol. vol. 560, No. 1, pp. 1-11 (2004).
Jsaon H. Mateika et al., "Intermittent Hypoxia and Respiratory Plasticity in Humans and Other Animals: Does Exposure to Intermittent Hypoxia Promote or Mitigate Sleep Apnoea", Exp. Physio., vol. 94, No. 3, pp. 279-296, Mar. 2009.
Ailiang Xie et al., "Influence of Arterial O2 on the Susceptibility to Post-Hyperventilation Apnea During Sleep", J. Appl. Physiol., vol. 100, pp. 171-177 (2006).
Kazuomi Kario, "Obstructive Sleep Apnea Syndrome and Hypertension: Mechanism of the Linkage and 24-h Blood Pressure Control.", Hypertension Research, vol. 32, pp. 537-541 (2009).
Amy S. Jordan et al., "Mechanisms used to Restore Ventilation After Partial upper Airway Collapse During Sleep in Humans", Thorax, vol. 62, pp. 861-867 (2007).
K. Dingli et al., "Arousability in Sleep Apnoea/Hypopnoea Syndrome Patients", Eur. Respir. J., vol. 20, pp. 733-740 (2002).
Magdy Younes, "Contributions of Upper Airway Mechanics and Control Mechanisms to Severity of Obstructive Apnea", Am. J. Respir. Crti. Care Med., vol. 168, pp. 645-658 (2003).
Ruzica Jokic et al., "Surface Tension Forces in Sleep Apnea: The Role of a Soft Tissue Lubricant", Am. J. Respir. Crit. Care Med., vol. 157-1522-1525 (1998).
Alan R. Schwartz et al., "Upper Airway Surface Tension: Is It a Significant Cause of Airflow Obstruction During Sleep?", J. Appl. Physiol., vol. 95, pp. 1759-1176 (2003).

(56) References Cited

OTHER PUBLICATIONS

Naresh M. Punjabi et al,. "Sleep-Disordered Breathing and Cardiovascular Disease An Outcome-Based Definition of Hypopneas", Am. J. Respir. Crit. Care Med., vol. 177, pp. 1150-1155 (2008).
Peter Kowallik et al., "Breath-to-Breath Variability Correlates with Apnea-Hypopnea Index in Obstructive Sleep Apnea", Chest, vol. 119, No. 2, pp. 451-459 Feb. 2001.
Amal M. Omran et al., "Posthypoxic Ventilatory Decline During NREM Sleep: Influence of Sleep Apnea", J. Appl. Physiol, vol. 96, pp. 2220-2225 (2004).
Krzysztof Narkiewicz et al., "Selective Potentiation of Peripheral Chemoreflex Sensitivity in Obstructive Sleep Apnea", Circulation, vol. 99, pp. 1183-1189 (1999).
Richard B. Berry et al., "Within-Night Variation in Respiratory Effort Preceding Apnea Termination and EED Delta Power in Sleep Apnea", J. Appl. Physiol., vol. 85, No. 4, pp. 1434-1441 (1998).
Gerhard Weinreich et al., "Pattern Recognition of Obstructive Sleep Apnoea and Cheyne-Stokes Respiration", Physiol. Meas., vol. 29, pp. 869-878 Jul. 4, 2008.
Melinda J. Carrington et al., "Blood Pressure and Heart Rate During Continuous Experimental Sleep Fragmentation in Healthy Adults", Sleep, vol. 31, No. 12, pp. 1701-1712 (2008).
Michael C. Hlavac et al., "The Effect of Hypoxia on Load Compensation During Sustained Incremental Resistive Loading in Patients with Obstructive Sleep Apnea", J. Appl. Physiol., vol. 103, pp. 234-239 (2007).
Danny J. Eckert et al., "Sustained Hypoxia Depresses Sensory Processing of Respiratory Resistive Loads", Am. J. Respir. Crit. Care Med., vol. 172, pp. 1047-1054 (2005).
Yaseen Arabi et al., "Daytime Blood Pressure Elevation After Nocturnal Hypoxia", J. Appl. Physiol., vol. 87, No. 2, pp. 689-698 (1999).
Anne Berssenbrugge et al., "Mechanisms of Hypoxia-Induced Periodic Breathing During Sleep in Humans", J. Physiol., vol. 343, pp. 507-524 (1983).
Ramon C. Hermida et al., "Evaluation of the Extent and Duration of the "ABPM Effect" in Hypertensive Patients", Journal of the American College of Cardiology, vol. 40, No. 4, pp. 710-717 (2002).
N.J. Ali et al., "The Acute Effects of Continuous Positive Airway Pressure and Oxygen Administration on Blood Pressure During Obstructive Sleep Apnea", Chest, vol. 101, pp. 1526-1532 (1992).
Eugene Nalivaiko et al., "Cardiac Changes During Arousals from Non-REM Sleep in Healthy Volunteers", Am. J. Physiol. Regul. Integr. Comp. Physio., vol. 292, pp. R1320-R1327 (2007).
V. Kaplan et al., "Detection of Inspiratory Flow Limitation During Sleep by Computer Assisted Respiratory Inductive Plethysmography", Eur. Respir. J., vol. 15, pp. 570-578 (2000).
Urs A. Leuenberger et al., "Short-Term Intermittent Hypoxia Enhances Sympathetic Responses to Continuous Hypoxia in Humans", J. Appl. Physiol., vol. 103, pp. 835-842 (2007).
Clodagh M. Ryan et al., "Periodicity of Obstructive Sleep Apnea in Patients with and without Heart Failure", Chest, vol. 127, pp. 536-542 (2005).
Thomas Brack et al., "Effect of Resistive Loading on Variational Activity of Breathing", Am. J. Respir. Crit. Care Med., vol. 157, pp. 1756-1763 (1998).
David W. Hudgel et al., "Instability of Ventilatory control in Patients with Obstructive Sleep Apnea", Am. J. Respir. Crti. Care Med., vol. 158, pp. 1142-1149 (1998).
David Schwartz et al., "On the Potential Clinical Relevance of the Length of Arousals from Sleep in Patients with Obstructive Sleep Apnea", J. Clin. Sleep Med., vol. 2, No. 2, pp. 175-180 (2006).
Vishesh K. Kapur et al., "Sleepiness in Patients with Moderate to Severe Sleep-Disordered Breathing", Sleep, vol. 28, No. 4, pp. 472-477 (2005).
Alexandros N,. Vgontzas et al., "Excessive Daytime Sleepiness in Sleep Apnea: It's Not Just Apnea Hypopnea Index", Sleep Med., vol. 9, No. 7, pp. 712-714, Oct. 2008.

Jason P. Kirknessa et al., "Upper Airway Obstruction in Snoring and Upper Airway Resistance Syndrome", Prog. Respir. Res. Basel, Karger, vol. 35, pp. 79-89 (2006).
Carlos Alberto Nigro et al., "Variation in the Duration of Arousal in Obstructive Sleep Apnea", Med. Sci. Monit., vol. 11, No. 4, pp. CR188-CR192, Apr. 2005.
Gang Bao et al., "Acute and Chronic Blood Pressure Response to Recurrent Acoustic Arousal in Rats", Am. J. Hypertens, vol. 12, pp. 504-510 (1999) (Abstract).
U. Leuenberger et al., "Surges of Muscle Sympathetic Nerve Activity During Obstructive Apnea are Linked to Hypoxemia", Journal of Applied Physiology, Aug. 1, 1995, vol. 79, No. 2, pp. 581-588 (Abstract).
Kazuo Eguchi et al., "Nocturnal Hypoxia is Associated with Select Cerebrovascular Disease in High-Risk Japanese Community-Dwelling Population", Am. J. Hypertens, vol. 18, pp. 1489-1495 (2005) (Abstract).
Ergun Onal et al., "Respiratory Timing During NREM Sleep in Patient with Occlusive Sleep Apnea", Journal of Applied Physiology, vol. 61, No. 4, pp. 1444-1448, Oct. 1, 1986.
Richard J. Martin et al., "Respiratory Mechanics and Timing During Sleep in Occlusive Sleep Apnea", Journal of Applied Physiology, vol. 48, No. 3, pp. 432-437, Mar. 1, 1980.
R.J. Davies et al., "Arterial Blood Pressure Responses to Graded Transient Arousal from Sleep in Normal Humans", Journal of Applied Physiology, vol. 74, No. 3, pp. 1123-1130, Mar. 1, 1993.
A. Schwan et al., "Effect on sleep—but not on blood pressure—of nocturnal non-invasive blood pressure monitoring", J. Hypertens, vol. 10, No. 2, pp. 189-194, Feb. 1992 (Abstract).
G. Parati et al., "Ambulatory Blood Pressure Monitoring does not Interfere with the Haemodynamic Effects of Sleep", J. Hypertens, vol. 3, No. 3, Nov. 1985 (Supplemental) (Abstract).
J.P. Degaute et al., "Does Non-Invasive Ambulatory Blood Pressure Monitoring Disturb Sleep", J. Hypertens, vol. 10, pp. 879-885 (1992) (Abstract).
M. Middeke, "Effect of Nocturnal Blood Pressure Measurement on Sleep and Blood Pressure During Sleep", Zeitschrift fur Kardiologie, vol. 85 Suppl 3, p. 99-105 (1996).
E. Fletcher, "Effect of Episodic Hypoxia on Sympathetic Activity and Blood Pressure", Respiration Physiology, vol. 119, No. 2-3, pp. 189-197 (2000) (Abstract).
U. Leuenberger, "Effect of Intermittent Hypoxia on Sympathetic Activity and Blood Pressure", Autonomic Neuroscience, vol. 121, No. 1, pp. 87-93 (2005) (Abstract).
Takuya Watanabe et al., "The Relationship Between Esophageal Pressure and Apnea Hypopnea Index in Obstructive Sleep Apnea-Hypopnea Syndrome", Sleep Research Online, vol. 3, No. 4, pp. 169-172 (2000) (Abstract).
M.S. Badr et al., "Post-Hyperventilation Hypopnea in Humans During NREM Sleep", Respiration Physiology, vol. 103, No. 2, pp. 137-145, Feb. 1996 (Abstract).
M.S. Badr et al., "Post-Hyperventilation Hypopnea in Humans During NREM Sleep", Respiration Physiology, vol. 103, No. 2, pp. 137-145, Feb. 1996.
Michael C. Khoo et al., "Ventilatory Dynamics During Transient Arousal from NREM Sleep: Implications for Respiratory Control Stability", Journal of Applied Physiology, vol. 80, No. 5, pp. 1475-1484, May 1, 1996.
J.J. Shin et al., "Fuzzy Assessment of Sleep-Disordered Breathing During Continuous Positive Airway Pressure Therapy", Sleep, vol. 12, No. 8, pp. 817-828, Dec. 15, 1998 (Abstract).
Garpestad et al., "Decrease in Ventricular Stroke Volume at Apnea Termination is Independent of Oxygen Desaturation", Journal of Applied Physiology, vol. 77, No. 4, pp. 1602-1608, Oct. 1, 1994.
C.P. O'Donnell et al., "Airway Obstruction During Sleep Increases Blood Pressure Without Arousal", Journal of Applied Physiology, vol. 80, No. 3, pp. 773-781, Mar. 1, 1996.
M.L. Smith et al., "Role of Hypoxemia in Sleep Apnea-Induced Sympathoexcitation", Journal of the Autonomic Nervous System, vol. 56, No. 3, pp. 184-190 (1996) (Abstract).

(56) References Cited

OTHER PUBLICATIONS

D.M. Carlson et al., "Acoustically Induced Cortical Arousal increases Phasic Pharyngeal Muscle and Diaphragmatic EMG in NREM Sleep", Journal of Applied Physiology, vol. 76, No. 4, pp. 1553-1559 (1994) (Abstract).
F. Raschke, "Arousals and Aircraft Noise—Environmental Disorders of Sleep and Health in Terms of Sleep Medicine", Noise Health, vol. 6, No. 22, pp. 15-26 (2004).
Joost G. van den Aardweg et al., "Repetitive Apneas Induce Periodic Hypertension in Normal Subjects Through Hypoxia", Journal of Applied Physiology, vol. 72, No. 3, pp. 821-827, Mar. 1, 1992.
Lamia Afifi et al., "Sleep and Respiratory Stimulus Specific Dampening of Cortical Responsiveness in OSAS", Respiratory Physiology and Neurobiology, vol. 136, No. 2-3, pp. 221-234, Jul. 16, 2003 (Abstract).
S.E. Martin et al., "The Effect of Nonvisible Sleep Fragmentation on Daytime Function", American Journal of Respiratory and Critical Care Medicine, vol. 155, No. 5, pp. 1596-1601, May 1997 (Abstract.
S. Miliauskas et al., "Peculiarities of Nocturnal Oxygen Saturation in Obstructive Sleep Apnea", Medicina (Kaunas), vol. 41, No. 3, pp. 217-220 (2005) (Abstract).
M.S. Badr et al., "Ventilatory Response to Induced Auditory Arousals During NREM Sleep", Sleep, vol. 20, No. 9, pp. 707-714 (1997) (Abstract).
D.W. Hudgel et al., "Alteration in Obstructive Apnea Pattern Induced by Changes in O2 and CO2 Inspired Concentrations", American Review of Respiratory Disease, vol. 138, No. 41, pp. 16-19, Jul. 1988 (Abstract).
H. Ye et al., "The Changes of Respiratory Mechanics in Patients with Obstructive Sleep Apnea-Hypopnea Syndrome During Sleep", Zhonghua Jei He He Hu Xi Ha Zhi, vol. 31, No. 1, pp. 26-31 (2008) (Abstract).
E.C. Fletcher, "Sympathetic Activity and Blood Pressure in the Sleep Apnea Syndrome", Respiration, vol. 64, Suppl. 1, pp. 22-28 (1997).
B.J. Morgan et al., "Neurocirculatory Consequences of Negative Intrathoracic Pressure vs. Asphyxia During Voluntary Apnea", Journal of Applied Physiology, vol. 74, No. 6, pp. 2969-2975, Jun. 1, 1993 (Abstract).
Concepcion Hernandez Garcia, "Sleep Apnea-Hypopnea Syndrome Without Excessive Daytime Sleepiness", Archivos de Bronconeumologia (English Edition), vol. 45, No. 5, pp. 240-244, 2009.
Neil S. Cherniack, "Apnea and Periodic Breathing During Sleep", N. Engl. J. Med., vol. 341, No. 13, pp. 985-987, Sep. 23, 1999.
W. De Backer, "Obstructive Sleep Apnea-Hypopnea Syndrome: Definitions and Pathophysiology", Sleep Apnea; Prog Resp. Res., Basel, Karger, vol. 35, pp. 90-96 (2006).
Transcript and screen shots of youtube video "NightShift Sleep Positioner", https://youtube/lq-2Uu8g3Pw, downloaded on Jul. 27, 2017.
"Nightshift Sleep Positioner" http://nightshifttherapy.com/ downloaded Jul. 27, 2017 (5 pages).
Product Brochure for NightShift Sleep Positioner, http://nightshifitherapy.com/ copyright 2013 (2 pages).
International Search Report issued in International Application No. PCT/US2015/059632, dated Mar. 30, 2016.
Written Opinion issued in International Application No. PCT/US2015/059632, dated Mar. 30, 2016.
Cherniack N.S., "Excitatory and Inhibitory Influences on the Ventilatory Augmentation Caused by Hypoxia", In: Lahiri S., et al., Response and Adaptation to Hypoxia, Total 7 pages, (1991).
Walsh DM, et al., "Transcutaneous electrical nerve stimulation for acute pain", Cochrane Database Syst Rev., vol. 2, Abstract only, Total 1 page, (Apr. 15, 2009).
Johnson MI, et al., "Transcutaneous electrical nerve stimulation for acute pain", Cochrane Database Syst. Rev., Issue 6, Total 97 pages, (Jun. 15, 2015).

Togo F., et al., "Electroencephalogram Characteristics of Autonomic Arousals During Sleep in Healthy Men", Clin. Neurophysiol, vol. 117, No. 12, Total 15 pages, (Dec. 2016).
Neckelmann D., et al., "Sleep stages and EEG Power Spectrum in Relation to Acoustical Stimulus Arousal Threshold in the Rat", Sleep, vol. 16, No. 5, pp. 467-477, (Aug. 16, 1993).
Ibanez, AM, et al., "ERPs Studies of Cognitive Processing During Sleep", International Journal of Psychology, vol. 44, No. 4, pp. 290-304, (Aug. 2009).
Muzet, A., "Environmental noise, sleep and health", Sleep Medicine Reviews, vol. 11, No. 2, pp. 135-142, (Apr. 2007).
Seifretz E., et al., "Auditory System Functional Magnetic Resonance Imaging. In Anatomic Basis Of Functional Magnetic Resonance Imaging", Neuroimaging Clinics of North America, vol. 11, No. 2, pp. 275-296, (May 2001).
Halasz P., et al., "The nature of arousal in sleep", J. Sleep Res., vol. 13, pp. 1-23, (Mar. 13, 2004).
Vasilios, P., et al., "Fractal Physiology, Breath-to-Breath Variability and Respiratory Diseases: An Introduction to Complex Systems Theory Application in Pulmonary and Critical Care Medicine"; Practical Applications in Biomedical Engineering, Total 27 pages, (Jan. 9, 2013).
Issa EB, et al., "Sensory Responses during Sleep in Primate Primary and Secondary Auditory Cortex", J. Neurosci., vol. 28(53), Total 34 pages, (Dec. 31, 2008).
Loewy DH, et al., "The mismatch negativity to frequency deviant stimuli during natural sleep", Electroencephalography and Clinical Neurophysiology, vol. 98, Issue 6, pp. 493-501, (Jun. 1996).
Purves, D., et al., "Excitatory and Inhibitory Postsynaptic Potentials", Neuroscience, 2nd Edition, Total 2 pages, (2001).
McEvoy, Doug, M.D., et al., "CPAP for Prevention of Cardiovascular Events in Obstructive Sleep Apnea", The New England Journal of Medicine, vol. 375, No. 10, pp. 919-931, (Sep. 8, 2016).
Guo J., et al., "Effect of CPAP Therapy on Cardiovascular Events and Mortality in Patients With Obstructive Sleep Apnea: A Meta-analysis", Sleep Breath, vol. 20, pp. 965-974, (Feb. 12, 2016).
Rosenberg, R., "Optimal Treatment of Obstructive Sleep Apnea and Excessive Sleepiness", Adv. Therapy, vol. 26(3), pp. 295-312, (2009).
Soose RJ, "Upper Airway Stimulation Therapy: A Novel Approach to Managing Obstructive Sleep Apnea", The Laryngoscope, vol. 126, pp. 55-58, (Sep. 2016).
Wray CM, et al., "Hypoglossal nerve stimulation for obstructive sleep apnea: A review of the literature", World Journal of Otorhinolaryngol Head Neck Surgery, vol. 2, pp. 230-233, (Dec. 22, 2016).
Bonnett, M., et al., "EEG arousals: Scoring rules and examples. A preliminary report from the Sleep Disorders Atlas Task Force of the American Sleep Disorders Association", Sleep, vol. 15, No. 2, pp. 173-184, (Jan. 1992).
Moro, M., et al., "Clinical predictors of central sleep apnea evoked by positive airway pressure titration", Nature and Science of Sleep, pp. 259-266, (2016).
Lehman, S., et al., "Central Sleep Apnea on Commencement of Continuous Positive Airway Pressure in Patients with a Primary Diagnosis of Obstructive Sleep Apnea-Hypopnea", Journal of Clinical Sleep Medicine, vol. 3, No. 5, pp. 462-466, (2007).
Javaheri, S., et al., "The Prevalence and natural History of Complex Sleep Apnea", Journal of Clinical Sleep Medicine, vol. 5, No. 3, pp. 205-211, (2009).
Eder, D., et al., "Detection and Analysis of Respiratory Airflow and Snoring Sounds During Sleep Using Laryngeal Sound Discrimination (LSD", IEEE, pp. 2636-2637, (1992).
Kisley, M.A., et al., "The effect of state on sensory gating: comparison of waking, REM and non-REM sleep", Clinical Neurophysiology, vol. 112, pp. 1154-1165, (2001).
Velluti, R.A., "Interactions between sleep and sensory physiology", J. Sleep Res., vol. 6, pp. 61-77, (1997).
BMJ Thorax, "Positive airway pressure for OSAHS", Journal of the British Thoracic Society, pp. 68-75, (2005).
Harvard, "Harvard University, Apnea: Understating the results", URL: http://healthysleep.med.harvard.edu/sleep-apnea/diagnosing-osa/understanding-results, Total 1 page. (Feb. 11, 2011).

(56) References Cited

OTHER PUBLICATIONS

U.S. Appl. No. 12/277,386.
U.S. Appl. No. 14/535,561.
U.S. Appl. No. 16/532,213.
Office Action issued in EP Application No. 15 856 295.9 dated Apr. 15, 2019.
Chinese Office Action issued in Chinese Application No. 201580072604.X dated Sep. 6, 2019.

* cited by examiner

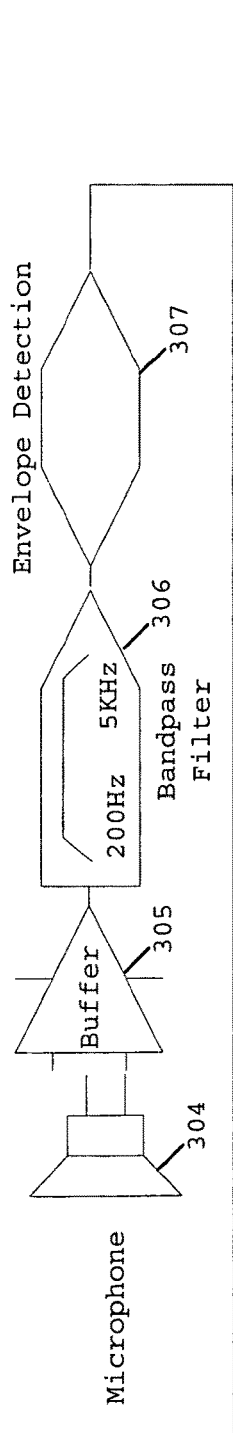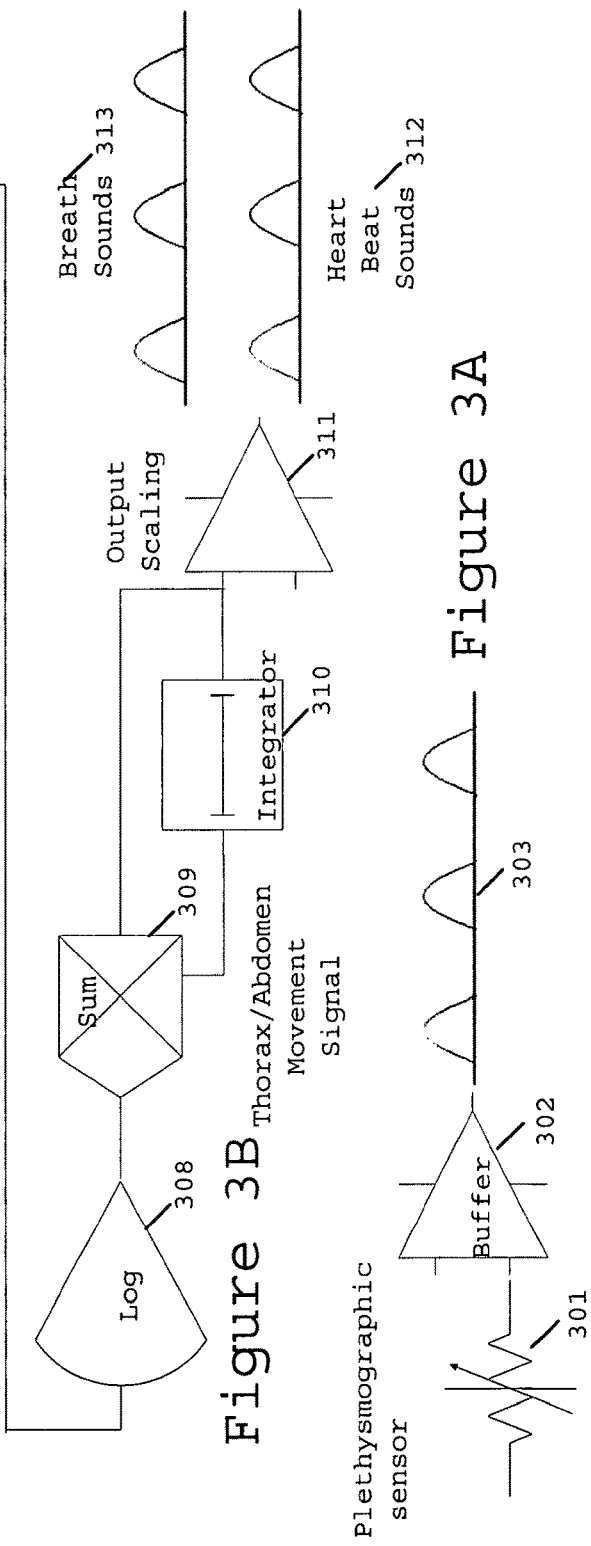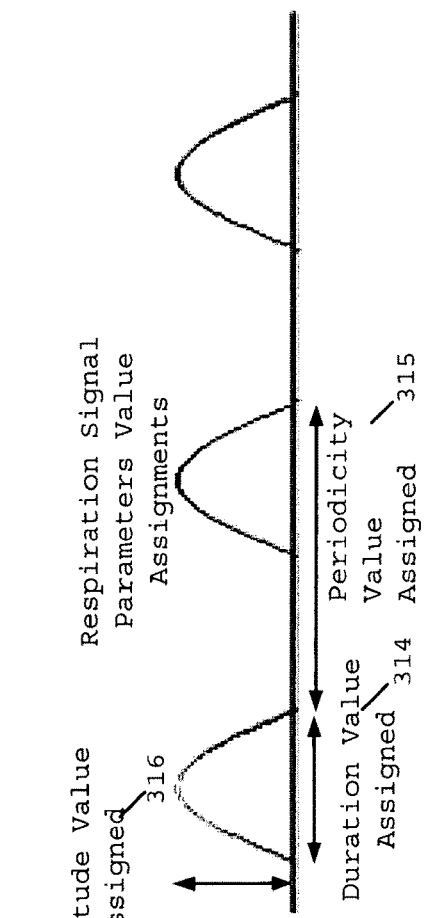

DEVICE TO DETECT AND TREAT APNEAS AND HYPOPNEA

CROSS REFERENCE TO RELATED APPLICATIONS

This application is a Continuation to U.S. patent application Ser. No. 12/277,386, filed Nov. 25, 2008, which claims the benefit of U.S. Provisional Application No. 60/990,035, filed Nov. 26, 2007, each of which are incorporated herein by reference in their entireties.

TECHNICAL FIELD

The present invention relates to an apparatus to detect and end occurrences of Sleep Apnea event and Hypopnea episode, in a manner that will decrease or eliminate hypoxia, hypercapnia and the disturbance of pulmonary hemodynamics Background Sleep Apnea and Hypopnea are breathing disorders that occurs during periods of sleep. It is an intermittent cessation or reduction of ventilation during sleep that results in a decrease in blood oxygen levels (hypoxia), increase in CO2 (hypercapnia), and vasoconstriction. The long term effects of these physiological changes are associated with the development of cardiac arrhythmias, congestive heart failure, cardiac ischemia, hypertension, heart disease, brain damage, and diabetes.

The causes of the various forms of Sleep Apnea and Hypopnea are not fully understood.

There are three general types of Sleep Apnea: Obstructive, Central and Mixed.

Obstructive Sleep Apnea (the most common type) is a blockage or occlusion of the oropharyngeal (upper) airway due to a loss of patency of its muscles. With Obstructive Sleep Apnea (OSA), respiratory functions continue as paradoxical movement of the thorax or abdomen. This paradoxical movement acts as a one way piston: air leaves the lungs but little or none can enter. The cause or causes of Obstructive Sleep Apneas is still a matter of much debate and research. The average Apnea event lasts 20 seconds however events of 2 to 3 minutes are not unknown. During the event, a number of physiological events occur. These include a vagal bradycardia, an increase in blood pressure, an increase in norepinephrine, and paradoxical respiratory efforts with increased respirator efforts. As an apnea event progresses, there is an increasing effort to breathe, increasing carbon dioxide (Hypercapnia), decreasing oxygen, and increasing level of proprioception. The longer the Apnea event, the more extreme these changes are.

At the end of an Apnea event tone (patency) returns to the upper airway muscles so that the upper airway suddenly re-opens. This can be associated with a sudden gasp or choking as air rapidly enters the lungs and surges in Heart Rate and Blood Pressure.

Information parsed from various research papers:

It has been believed that an arousal from a deeper stage of sleep to a lighter stage of sleep was required to terminate an Apnea episode; however studies have cast doubt on that assertion: "In summary, in the vast majority of patients, if not in all patients, arousal is required neither to initiate UA (Upper Airway) opening nor to obtain adequate flow. UA opening would occur at approximately the same time regardless of when or whether arousal occurs and the flow response in most patients would still be timely and adequate. Arousals are incidental events that occur when the thresholds for arousal and arousal-independent opening are close to each other, as they appear to be in patients with OSA. By promoting an unnecessarily high flow response at UA opening, arousals help perpetuate cycling and likely exacerbate OSA." (YOUNES, Magdy. Role of Arousals in the Pathogenesis of Obstructive Sleep Apnea. American Journal of Respiratory and Critical Care Medicine: Mar. 1, 2004. Role of Arousals in the Pathogenesis of Obstructive Sleep Apnea. Which is hereby incorporated by reference.

Although cortical activation is the gold standard for definition of arousal, several studies show there are different levels of central nervous system activation. At the lower range of arousal responses are those inducing reflex motor responses, autonomic activation, and appearance of slow wave EEG activity, i.e., delta bursts (D-bursts) and K-complex bursts (Kbursts), all defined as "subcortical arousals." At the upper range are arousal responses implying a cortical activation represented by MA6 and phases of transitory activation (PAT).

These findings might corroborate the hypothesis of the existence of 2 separate neural systems integrated in the arousal network and undergoing different modulatory influences."

Further studies indicate that overall, increasing ventilatory effort may be the most important stimulus to arousal from sleep, and the stimulus to arousal from hypoxia and hypercapnia may be mediated principally through stimulating an increased ventilatory efforts.

These considerations raise the question of possible manipulation of the arousal response to maximize the beneficial effects related to facilitating resumption of airflow, but minimize the adverse consequences related to sleep fragmentation and post-apnea hyperventilation. These latter effects appear to relate more to cortical than brainstem arousal.

Furthermore some studies concluded that: "The current findings suggest that strategies of induced arousal, at an intensity level stimulating respiration while avoiding recruitment of the ascending arousal system and its potential effects of sleep disruption, could have potential application as a therapeutic modality. Apnea was detected by tracheal breath sounds which were picked up by microphone . . . stimulation decreased the frequency of apnea episodes and the longest apnea duration. This resulted in an increase in arterial oxygen saturation. Moreover stimulation decreased sleep stages I and II, and increased stages III and IV. These findings suggest that stimulation using the apnea demand-type stimulator may be an effective treatment for OSA."

Other research has determined that: the Psa (Blood Pressure) and HR (Heart Rate) increased more and the SV (Stroke Volume) decreased more in the apnea that was terminated by an EEG (cortical) arousal compared with the apnea without an EEG (subcortical) arousal.

Furthermore externally applied stimulus is reported to cause a "trend among our subjects to shortening of the apnea immediately after the stimulated apnea; that is, the effect of the tone appeared to extend to the next apnea. We would hypothesize that the acoustic stimuli did alter sleep state and thus arousal threshold such that the immediately succeeding apnea might have been more susceptible to concurrent respiratory afferent stimuli".

This took place in spite of the trend for Obstructive Sleep Apneas to increase in both frequency and duration during a nights sleep.

"Using sound stimulation with 90-dB tones at 625 Hz, 1/1 to 1/5 min rate delivered by headphones, Levine et al. (1987) found that the number of natural arousals decreased during nights with frequent (1/1 min) stimulation resulting into abundant evoked arousals." (Halasz 2004)

"One animal study reported that the [stage two slow wave sleep] SWS-2 (in rats), with high delta wave power, showed the highest arousal threshold when a non-meaningful sound was used (Neckelmann and Ursin 1993)." (Velluti 1997)

"Conflicting results have been reported concerning sound stimulation effects on sleep in animals. Continuous high intensity white-noise stimulation resulted in almost complete deprivation of [paradoxical sleep] (PS) in rabbits (Khazan and Sawyer 1963) while Kleitman (1963) observed that nystagmus is greatly reduced in rats, the same stimulation led to PS reduction without a or even abolished during sleep. Associated with this, it was decrease in the amount of [slow wave sleep] (SWS) (Van Twyver et al. 1966)." (Velluti 1997)

"Very interesting results were reported by Buendia et al. (1963) who observed that the responsiveness of a conditioned cat to a 5 kHz 'positive' tone (reinforced with classical and instrumental conditioning) during wakefulness was characteristic but different in each sleep phase, measured by the tone's capacity to awaken the animal" (Velluti 1997)

"The K-complex response to auditory (click) stimulation is large and less variable during light sleep (stage 2); while during stage 4 SWS there is no sensory-evoked modifications of the electrical activity." (Velluti 1997)

"The amplitude of the averaged auditory nerve compound action potential and the microphonic potentials, in response to clicks and tone-bursts, have been reported to change throughout the sleep/waking cycle." (Velluti 1997)

"80% of the recorded cells changed their firing during binarual stimulation while 85% did so during ipsilateral sound stimulation. In addition, shifts in the discharge pattern were observed in 15% of the cells recorded on passing from W to sleep while the most striking change, observed in decreasing firing units, was the near-absence of responses in PS during the last 40 ms as judged from the post-stimulus time histogram (stimuli: 50-ms tonebursts)." (Velluti 1997)

"The organization of human sleep is extremely sensitive to acoustic stimuli and noise generally exerts an arousing influence on it." (Velluti 1997)

The kind of stimuli provokes different responses in human subjects: "Previous studies using single-modality paradigm have shown that sensory gating systems, which select relevant sensory information, remain functional during sleep In humans, relevant stimuli (e.g. sound >65 dB, one's own name, experimental noxious stimulation) induce arousal response more frequently and results in more intense response compared with irrelevant stimuli. Simultaneous multi-modality sensory inputs from body surface and from other organs (e.g. ear) not only increase the amount of sensory inputs but also can maximize the relevance of stimuli". HALA" sz et al., 2004; Kisley et al., 2001; Velluti, 1997, which is hereby incorporated by reference.

Central Sleep Apnea results from the brain failing to signal the muscles to breathe. The neural drive to the respiratory muscles discontinues for a brief period of time. These transients may continue throughout the night for periods from ten seconds to as long as 2 to 3 minutes. The physiological effects are similar to those of Obstructive Sleep Apnea.

Mixed Sleep Apnea is a combination of Obstructive Sleep Apnea and Central Sleep Apnea.

There are several known treatments for Sleep Apnea. They consist of physical, electrical, and mechanical methods, surgery, and attempts at pharmacological treatment. The treatment regimen is tailored to the individual, and is based on the medical profile of the patient being treated.

The most common effective treatment for patients with sleep apnea is nasal continuous positive airway pressure (CPAP). In this form of treatment, the patient wears a mask over the nose while sleeping. The mask is connected to a compressor that creates a positive pressure in the nasal passages. The continuous positive airway pressure system prevents the airway from closing or becoming obstructed during sleep. The air pressure from the continuous positive airway system is constant, and can be adjusted to best suit the individual's apnea condition. The air pressure in the continuous positive airway pressure system must be adjusted so that it maintains an open airway in the patient during all periods of sleep, but does not provide excessive pressure such that the device is bothersome to the patient. U.S. Pat. No. 4,655,213 discloses sleep apnea treatments based on the principles of continuous positive airway pressure. There have also been recent attempts at varying the applied pressure to increase the effectiveness of continuous positive airway pressure treatment. U.S. Pat. Nos. 4,773,411 and 6,539,940 disclose such techniques. The disclosures of these United States patents are incorporated herein by reference.

Another treatment for sleep apnea in certain patients involves the use of a Dental Appliance to reposition oral structures such as the tongue and the lower jaw. This form of treatment is typically performed by a dentist or dental specialist such as an orthodontist.

Surgery has also been performed to treat sleep apnea. In some surgical treatments, the size of the airway is increased. These surgical procedures contain elevated levels of risk in comparison to other treatment methods, and often times are not entirely effective. The form of surgery to be undertaken is specific to the patient and the patient's medical profile. The removal of obstructive tissue in the airway such as adenoids, tonsils or nasal polyps is a common form of surgical treatment for sleep apnea. The surgical correction of structural deformities is also a common form of surgical treatment for sleep apnea.

Another form of surgical treatment for sleep apnea is uvalopalatopharyngoplasty. This procedure removes excess tissue from the back of the throat, such as tonsils, uvula, and part of the soft palate. Somnoplasty is also being investigated as a possible treatment for sleep apnea. Somnoplasty uses radio waves to reduce the size of some airway structures such as the uvula and the back of the tongue.

Other forms of surgical intervention for sleep apnea include maxillo-facial reconstruction. Another form of surgical treatment for patients with severe and life threatening sleep apnea is Tracheostomy. This procedure involves making a small hole in the windpipe that accommodates a tube. The tube is opened only during sleep, and allows a patient to take air directly into the lungs, effectively bypassing any upper airway obstructions. Tracheostomy is an extreme procedure that is very rarely used except for cases of imminent life threatening sleep apnea.

Attempts at pharmacological treatment for sleep apnea have included respiratory stimulants such as theophylline, acetazolamide and medroxy-progesterone, and adenosine. Drugs that stimulate brain or central nervous system activity, such as naloxone and doxapram, have also been used in an attempt to treat sleep apnea. Other drugs that act on the neurotransmitters involved with respiration have also been used in an attempt to treat sleep apnea. These drugs include serotonin, dopamine, tryptophan, fluoxetine, and others.

More recently, systems have been developed for the purpose of clearing upper airway passages during sleep using the electrical stimulation of nerves or muscles. In some cases, these systems require surgical implantation of sensors and associated electronics that detect when breathing has ceased and then stimulate the breathing process. Some hybrid systems have been developed that require surgical insertion of one or more sensors plus external equipment for monitoring the breathing process or moving the obstruction when breathing ceases.

An apparatus has been patented a means for detecting the onset of a sleep related disorder using pulse rate and blood oxygen content information as measured by the device; U.S. Pat. No. 7,387,608 discloses sleep apnea treatments based on those principles. The disclosures of these United States patents are incorporated herein by reference.

An apparatus has been patented a means for detecting the onset of a sleep related disorder using a multiplicity of microphones. The apparatus has the microphones emplaced within a collar worn around the neck of the patient. The apparatus detects breathing sounds, and in an embodiment when it detects breathing that is "substantially different from the recorded at least one signal pattern that is associated with a normal breathing pattern of the person; and creating a stimulus to the person's neck muscles to cause the person to move the person's neck muscles to move the person's head backwards to restore normal breathing before cessation of breathing occurs", as disclosed in U.S. Pat. No. 6,935,335. The disclosures of these United States patents are incorporated herein by reference.

SUMMARY OF THE INVENTION

The present invention is directed to a apparatus and method for detecting and treating Sleep Apnea and Hypopnea by terminating a Sleep Apnea event or Hypopnea episode within seconds of detection.

The invention develops through a Method a Referential set of Parameters specific to the respiration patterns of the specific patient (rather than defining and applying Generic Trigger point Parameter as is the case with other inventions). The multiplicity of Signal Parameters combined with a Fuzzy Control System is more adaptable to the changes of Respiration that occurs during the course of the night. Changes of Respiration which might be interpreted by other inventions such as those who use averaging or weighted moving averaging of invention and determined to be a reversion to a Respiration pattern that is normal for this specific patient. Normal for the patient is established by the Processing of the Referential set of Parameters within the Fuzzy Control System.

The inventions method of using both the root-mean-square deviation of a parameter and the parameters' mean, as opposed to simply averaging or weighted moving averaging of the parameter, to establish a reference point for determination of a parameters' out of bound condition, is a superior method for detecting Apnea events or Hypoxia episodes.

In accordance with the present invention, there is provided a wearable, belt like, apparatus for the treatment of Sleep Apnea events and Hypopnea episodes containing a Microphone and a Plethysmograph. The Microphone and Plethysmograph generate signals that are representative of physiological aspects of respiration. The signals are transferred to an embedded computer. The embedded computer extracts the sound of breathing and the sound of the heart beat by the means of Digital Signal Processing techniques. The embedded computer has means for determining when respiration parameters falls out of defined boundaries for the respiration parameters. This method is for the real-time detection of the onset of a Sleep Apnea event or Hypopnea episode. The embedded computer supplies stimulation signals upon the determination of a Sleep Apnea event or Hypopnea episode to initiate an inhalation. The stimulation is provided in a manner so as to avoid the initiation of a cortical (EEG) arousal and vagal withdrawal of the parasympathetic tone to the heart. The stimulus is applied to the patient by a cutaneous rumble effects actuator and audio effects broadcasting. The actuator is embedded within the invention.

It is a primary object of the present invention to provide a system and method for detecting and terminating an Sleep Apnea event and Hypopnea episode, within seconds of the detection, in a manner that will decrease or eliminate hypoxia, hypercapnia and the disturbance of pulmonary hemodynamics respirations as an Apnea Event or Hypopnea episode could be processed by the present invention.

Technical Problem

Positive Airway Pressure (PAP) systems remain the most effective treatment for sleep apnea. Many patients, however, cannot tolerate the Positive Airway Pressure systems and associated apparatus. Common complaints include discomfort with the applied pressure, discomfort with the mask and equipment, nasal irritation, nasal stuffiness and congestion, airway dryness, mask air leaks and noise, entanglement, claustrophobia, noise of the PAP machine, headaches, abdominal bloating, sore and irritated eyes, and an overall discomfort with the machinery. The noise and general obtrusiveness of the PAP apparatus are often disruptive to another person sleeping with the user.

A significant minority of the people for whom PAP is prescribed (estimated to be 30% to 50%) refuse to use it. A study determined that of the patients who use PAP treatment, it is estimated that 34% use it intermittently (4 nights per week) and/or remove it for part of the night (for this group median nightly usage is 3.1 hours).

Beyond the initial cost of the PAP (>U$500.00) there is a continuing cost of replacement masks. It is recommended that masks be replaced every six months (=>U$100.00/mask).

A study determined that Dental Appliances was successful in treating OSA in an average of 52% of treated patients, with success defined as no more than 10 apneas or hypopneas per hour of sleep. Treatment adherence is variable with patients reporting using the appliance a media of 77% of nights at 1 year.

A Dental Appliance typically has a cost in excess of U$1000.00.

Surgery has inherent risks: its' cost is high, its' success rates vary and over a period of time its' effectiveness fades.

Pharmacological treatments for sleep apnea have not achieved any consistent levels of effectiveness, and often contain side effects.

Systems that clear the upper airway passages during sleep using the electrical stimulation of nerves or muscles. These systems may produce positive results but they also have associated risks due to surgery, may need replacement at later times (requiring additional surgery), and may have higher costs and lower reliability than the more traditional treatments. In addition, the hybrid systems also have the accompanying physical restrictions and accompanying disadvantages associated with connections to the external equipment.

An apparatus whose means for detecting the onset of a sleep related disorder relies on blood oxygen content information cannot determine the onset of a sleep order in real time. Oxygen saturation level diminishment always lags the cessation of breathing because it takes time for the as oxygen in the bloodstream to used up by bodily processes. Hypoxia and hypercapnia will occur.

An apparatus whose sole means for detecting the onset of a sleep related disorder relies on detecting the sounds of breathing can be confused by extraneous noises, coughing, wheezing and other internally generated biologic noises. In addition in order for both the microphones and stimulus devices to work most effectively they must be in close contact with the neck and this constriction may prove to be unacceptably uncomfortable to the patient.

Many of these devices provide a single type of auditory stimulus (a fixed tone of varying intensity) and/or mechanical stimulus (a vibrator).

For example, U.S. Pat. No. 7,387,608 discloses such techniques. It is Claimed that: "The method of arousing the patient from sleep at the onset of a sleep apnea event will decrease or eliminate the occurrence of sleep apnea, arrhythmia, and partial epilepsy over time."

These methods of stimulus may prove to be initially effective in reducing the numbers of Apnea events through a process of Conditioning. However, with Conditioning there co-exists Habituation. These are two interacting psychological phenomena with a number of similarities. In Conditioning, an animal is exposed to some events, and as a consequence, it learns to associate a certain behavior with a specific situation. In Habituation too, an event occurs repeatedly, but in this case, the reaction of the animal wanes with repeated exposure.

The dynamics of Habituation is very similar to the extinction of a response that has previously been learned during Conditioning. In both cases, the response becomes less probable or weaker with each occurrence with the event. There is one large difference between the two situations, however. In extinction, a learned response is weakened, but in Habituation the reaction that dies away is typically an innate orienting reaction. Conditioning may indeed lead to extinguishment of Sleep Apneas events or the opposite may occur; Habituation might lead to the patient ignoring the stimulus. If Habituation occurs then Sleep Apnea events would continue until they spontaneously terminate.

Solution to Problem(s)

Therefore, there is a need in the art for an improved system and method for treating Sleep Apnea events and Hypopnea episodes. In particular, there is a need in the art for a system and method that does not create other types of sleep disturbing effects, does not require surgical implementation, does not involve the use of a complicated apparatus, does not include the use of pharmaceuticals, does not require the intervention of health professionals, and does not have the high costs associated with some of the types of treatments currently in use.

Therefore, there is a need for a system and method for treating Sleep Apnea event and Hypopnea episode by terminating a Sleep Apnea event and Hypopnea episode in real time that minimizes the disturbance to pulmonary hemodynamics.

Therefore, there is a need for a system and method for treating Sleep Apnea event and Hypopnea episode that is easy to use by the patient, comfortable, and less expensive than other methods of treatment.

Advantageous Effects of Invention

An Advantageous Effect of Invention is the superior method of detection of Sleep Apnea events and Hypopnea episodes:

Using the standard deviation of a parameter in conjunction with the parameters' mean and a rules based processing (Fuzzy Logic) as opposed to using only a parameters' mean as a reference point for determination of a parameters' out of bound condition (excursion) leads to the diminishment of the occurrence of the invention detecting a false Apnea event or Hypoxia episode.

In the situation where the parameters' mean is the only reference, a single excursion beyond an established limit leads declaration of an Apnea event or Hypoxia episode. Conversely, with this method of the invention, when an excursion is determined, a further determination is performed to establish if the excursion is smaller than every member of the set of parameters that were gathered during the Self-calibrations processes. For while an excursion might be smaller than the mean of the parameter that was calculated by the processes the Self-calibrations, it might be greater than any single parameter that formed the set of parameters that were determined to be "normal" for this specific patient and which formed the reference set of parameters.

The use of rules based processing (Fuzzy logic) allows the invention to evaluate the significance of excursions and make decisions as to whether as excursion merits initiating Stimulus.

The invention analyzes a multiplicity of parameters derived from redundant apparatus to detect respirations. The use of rules based processing (Fuzzy logic) allows the invention to evaluate the significance of excursions of any single parameter or any combination of parameters from the redundant apparatus and make decisions as to whether as excursion merits initiating Stimulus.

Another Advantageous Effect of the Invention is its' ease of use. Many of the patients who would use the invention are both obese and old(er). The invention is simple to don. The invention uses plain language commands to guide the patient in to properly position the invention.

Another Advantageous Effect of the Invention is it is not an encumbrance. The sleeping patient is not physically constrained. This is important in light of the fact that many of the patients have enlarged prostrates which, in many cases, necessitates frequent urination during the night.

Another Advantageous Effect of the Invention is that it is less expensive that most other solutions. From the perspective of overall costs:

It does not require the programming of baseline parameters. Baseline parameters that have to be entered into an apparatus would require that there be an evaluation of the results from the patients' polysomnography and using a method to establish baseline criteria. The invention self determines the baseline parameters.

There are no replacement components. Other devices require periodic replacement of key components, at a considerable expense.

The invention is no more expensive that the average price of the most popular form of treatment for Obstructive Sleep Apnea (CPAP).

Another Advantageous Effect of the Invention is that it can be used in conjunction with the most popular form of treatment for Obstructive Sleep Apnea (CPAP) or as an alternate, independent form of treatment. There is a significant minority or patients who use the CPAP intermittently.

Using the invention during those times that the patient is not using CPAP would continue the benefit to the patient that is realized by maintaining normal blood oxygen and carbon dioxide levels.

Another Advantageous Effect of the Invention is it is self-adapting; it self-determines referential baselines for the specific patients' normal respiration patterns. One of the definitions of Obstructive Sleep Apnea is interruptions in airflow of at least 10 seconds. The invention may, depending on the normal respiration pattern of that patient, establish a different baseline as to what an interruption of airflow in seconds would be.

By immediately applying a Stimulus that has been determined to initiate an inhalation at the lowest level of stimulation, the effects on the physiology of the patient of the Apnea event or Hypoxia episode will be minimized.

Another Advantageous Effect of the Invention is that there are devices that ramp up the stimulus (be it the frequency of a mechanical vibrator and/or audio and/or amplitude) until respiration is restored. This takes time, in which case the deleterious effects of declining blood oxygen and increasing blood carbon dioxide accrue, and if it overshoots (there being a delay between the time a stimulus is applied and the reaction of the patient to it) it could lead to a heightened waking than is required to terminate the Apnea event or Hypoxia episode.

Another Advantageous Effect of the Invention is that it is self-adapting; it self-determines referential baselines for the type of Stimulus that is required to terminate an Apnea event or Hypoxia episode. Research has shown that the amount of stimulus required to initiate an inspiration changes in cycles during sleep. The invention continuously evaluates the Stimulus required to terminate an Apnea event or Hypoxia episode.

Another Advantageous Effect of the Invention is that it can supply a very wide range of Stimulus. It has a multiplicity of embedded Audio files and Haptic pattern files, each with a distinct irritation index. The invention will determine which files produce the Stimulus required to initiate an inhalation at the lowest level stimulation. Since there are many file combinations that will produce the Stimulus required to initiate an inhalation at the lowest level stimulation, the invention can avoid Habituation while maintaining the benefit of Conditioning.

BRIEF DESCRIPTION OF DRAWINGS

The invention will be described by reference to the following drawings, in which like numerals refer to like elements, and in which:

FIGS. 3A, 3B, and 3C are Block Diagrams of the manner in which Microphone and Plethysmographic sensor data is converted into Signals;

DESCRIPTION OF EMBODIMENTS

Figure 1:
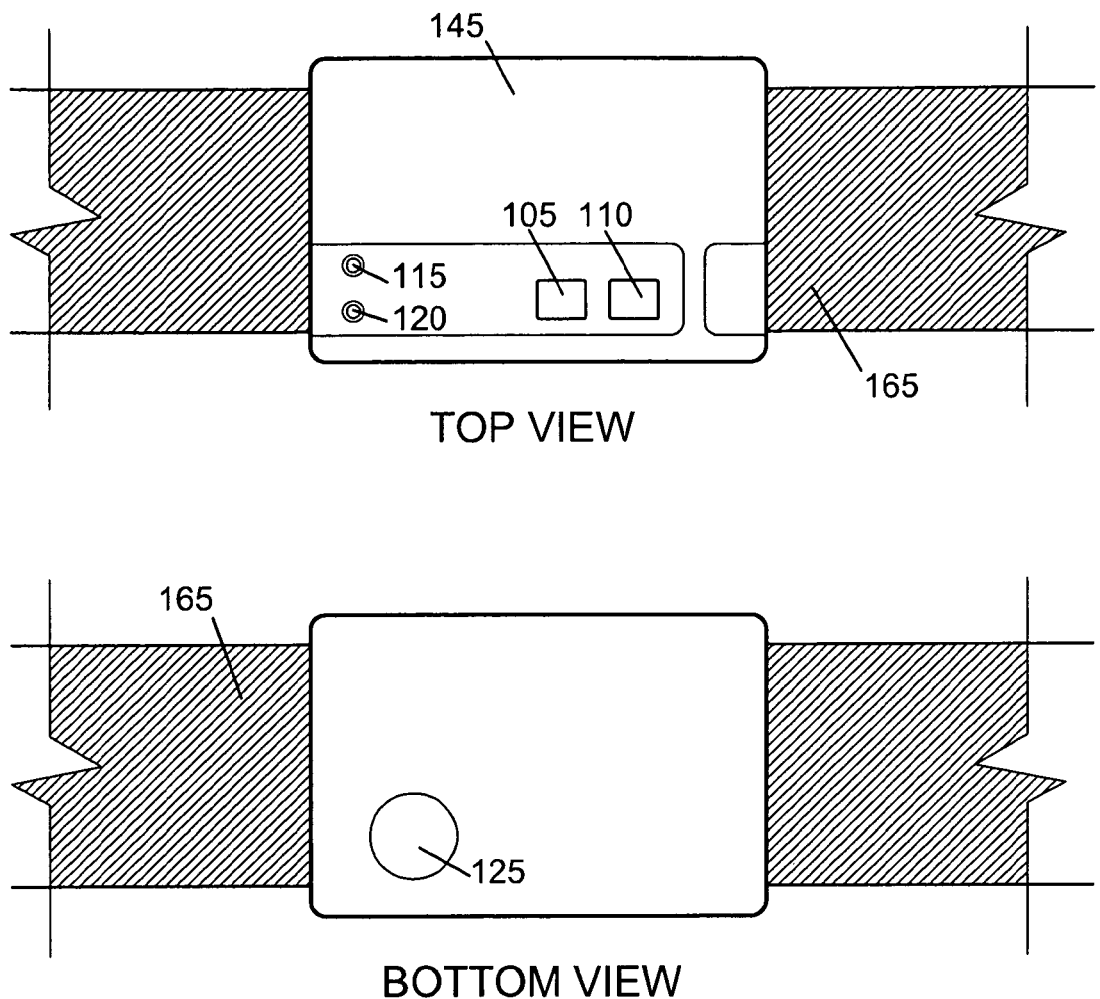
FIG. 1 is a top and Bottom External view of the present invention.

Accordingly, embodiments of the present invention are provided that meet at least one or more of the following objects of the present invention.

In one embodiment, a wireless auditory prompter(Bluetooth Earbud) is mounted in the patient's ear and is activated by the stimulation signal to emit an acoustic stimulus which is heard by the patient but is inaudible to others. This embodiment provides a sound to initiate inhalation without requiring other intervention.

In another embodiment, a wired auditory prompter is mounted in the patient's ear and is activated by the stimulation signal to emit an acoustic stimulus which is heard by the patient but is inaudible to others. This embodiment provides a sound to initiate inhalation without requiring other intervention.

In another embodiment, a loud speaker is embedded within the invention and is activated by the stimulation signal to broadcast an acoustic stimulus which is heard by the patient. This embodiment provides a sound to initiate inhalation without requiring other intervention.

In another embodiment, the computer detects the absence of a heartbeat and activates an audible alarm by the loudspeaker embedded within the present invention.

In another embodiment, the computer has means to store the calculated amplitude, periodicity, and duration of respiration for each respiration of the collection of known good respirations from the first self-calibration in imbedded memory.

In another embodiment, the computer has means to store the calculated values and parameters in imbedded memory.

In another embodiment, the computer has means to store the time(s) in which a Sleep Apnea event and Hypopnea episode occurs in imbedded memory. In another embodiment, the computer has means to store the time(s) in which a Sleep Apnea event and Hypopnea episodes are terminated in imbedded memory.

In another embodiment, the computer has means to export the calculated values and parameters from imbedded memory to other devices.

In another embodiment, the computer has means to export the time(s) in which a Sleep Apnea event and Hypopnea episode occurs and from imbedded memory to other devices.

In another embodiment, the computer has means to export the time(s) in which a Sleep Apnea event and Hypopnea episode are terminated from imbedded memory to other devices.

In another embodiment, the computer has means to import modifications of the computer programs from other devices.

In another embodiment, the computer has means to import modifications of the computer program that comprises the rules based processing (Fuzzy Logic) from other devices.

In another embodiment, the plethysmographic sensor can be implemented using a string potentiometer.

In another embodiment, the plethysmographic sensor can be implemented using strain gauges.

In another embodiment, the plethysmographic sensor can be implemented using accelerometers.

In another embodiment, the plethysmographic sensor can be implemented using Hall Effect components.

In another embodiment, the plethysmographic sensor can be implemented using LEDS and Photo detectors.

In another embodiment, the plethysmographic sensor can be implemented using ultrasonic sensors.

In another embodiment, there might be a plurality of microphones.

In another embodiment, the mechanical tactile sensory stimulator may be implemented using a Haptic Display.

In another embodiment, the mechanical tactile sensory stimulator maybe implemented using a Haptic Display comprising shape memory springs.

In another embodiment, the mechanical tactile sensory stimulator maybe implemented using a Haptic Display using multiple actuators.

In another embodiment, the mechanical tactile sensory stimulator maybe implemented using a Haptic Display comprising rotating drums.

In another embodiment, the mechanical tactile sensory stimulator maybe implemented using a Haptic Display comprising electroactive polymers.

In another embodiment, sensory stimulation may be applied optically by the donning of a device that is worn over the eyes and in which LEDs shine light through the eyelids into the pupils.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description, it may be advantageous to set forth definitions of certain words and phrases used throughout this patent document: the terms "include" and "comprise" and derivatives thereof mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware, or software, or some combination of at least two of the same. Definitions for certain words and phrases are provided throughout this patent document. Those of ordinary skill in the art should understand that in many, if not most, instances, such definitions apply to prior, as well as future uses of such defined words and phrases.

"Measurement" by the Computer in this application is defined as an Analog-to-Digital Conversion. The derivative of Analog-to-Digital Conversion is a numeric value that is representative of the Signals Amplitude at the time that the Measurement is made. Those skilled in the art will understand the method of using Analog-to-Digital conversion.

"Processing", "Process", "Monitoring", and "Method" are used interchangeably in this document and are collectively defined as the application of software programs that are resident within the Computer as means or manner of procedure to accomplishing something. The means and reasons for the Processing will be addressed in detail within this document.

"Stationary" or "quasi-stationary" signals are those in which the statistical distribution of frequencies does not change significantly over the time scale of interest.

"Nonstationary" signals are those whose statistical frequency distribution changes significantly over the time scale of interest.

"Naturalistic" sounds are sounds that are naturally-occurring or that mimic naturally-occurring sounds. Naturalistic sounds are nonstationary and have logarithmically distributed spectrotemporal modulations, as compared with the linearly distributed spectrotemporal modulations of sounds that are not naturalistic.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

For a general understanding of the present invention, reference is made to the drawings. In the drawings, like reference numerals have been used throughout to designate identical elements.

In accordance with this present invention, there is provided an apparatus and method for the diagnosis and treatment of Sleep Apnea and Hypopnea. In one embodiment of the invention, the respirations of the patient are monitored during sleep by the apparatus, which acts as a monitoring system to detect and treat Sleep Apnea events and Hypopnea episodes in the patient. The monitoring system is comprised of an integrated plethysmographic, an integrated microphone, an integrated computer and software program, and methods for applying stimulus to the patient such as an integrated loud speaker, wired and wireless audio, and an integrated rumble effects actuator. The invention is a wearable, belt-like device, the device is fitted around the Thorax or Abdomen of a patient.

At the onset of a Sleep Apnea event or Hypopnea episode the respiratory induced movement (expansion and contraction) of the Thorax and/or Abdomen are significantly reduced. In addition, the movement of air into the lungs is significantly reduced. These decreases are indicators of an onset of a Sleep Apnea event or Hypopnea episode. During sleep, it is normal for the patients' respiration parameters for amplitude, periodicity, and duration of respiration to vary. Discerning between those normal variations in the parameters (for amplitude, periodicity, and duration of respiration during sleep) and abnormal variations in parameters (for amplitude, periodicity, and duration of respiration levels), is performed using a software program that compares those parameters gathered by monitoring parameters (for amplitude, periodicity, and duration of respiration during sleep) to those parameters (for amplitude, periodicity, and duration of respiration) gathered before the patient fell asleep. This method accurately identifies the onset of a Sleep Apnea event or Hypopnea episode and eliminates false determinations.

The embedded computer's software program uses rules based processing (Fuzzy Logic) to determine when Stimulation is to be applied in order to restore airway patency (by inducing inspiration).

When the patient's respiration parameters are determined by the rules based processing (Fuzzy Logic) as showing the onset of an Sleep Apnea event or Hypopnea episode Stimulation is provided.

The present invention may use historical data, software programs, algorithms or subroutines to assist with the determination of the rules based processing (Fuzzy Logic) that are appropriate to the patient. The embedded computer's software program uses rules based processing (Fuzzy Logic) to determine the least amount of Stimulation required to induce inspiration.

The Stimulation is in the form of audio signals and by a cutaneous rumble effects actuator. Rules based processing (Fuzzy Logic) determine the least amount of Stimulation required to induce inspiration.

FIGS. 1 through 8, discussed below, and the various embodiments used to describe the principles of the present invention in this patent document are by way of illustration only and should not be construed in any way to limit the scope of the invention. Those skilled in the art will understand that the principles of the present invention may be implemented in any suitably modified system for detecting and terminating an obstructive sleep apnea event.

FIG. 1 illustrates one embodiment of the present invention showing External views, Top and Bottom.

The embodiment of the present invention that is illustrated in FIG. 1 has Microphone 125 capable of detecting sounds within the airway of patient (not shown). One type of microphone that is suitable for use in the present invention is the electret microphone. Microphone 125 is attached to the Housing 145 and Housing 145 is detachably fastened around the Thorax or Abdomen of the patient (not shown) with a Belt 165 and Velcro clasp (not shown in FIG. 1). Housing 145 is fastened around the Thorax or Abdomen of the patient (not shown) so that Microphone 125 is positioned adjacent to the lungs and in contact with the patient (not shown on FIG. 1).

LEDs 115 & 120 are Status indicators. The emitted color that the LEDs display are indicative of operational conditions of the present invention.

Buttons 105 & 110 control the operations of the present invention.

The Microphone 125 is capable of generating signals representative of the sounds of breathing of person 120. When Microphone 125 detects sounds of breathing, it generates a signal. The signal generated by the Microphone 125 is transferred via an individual microphone signal line to signal processing circuitry 200 (shown in FIG. 3) contained within Housing 145.

Figure 2:
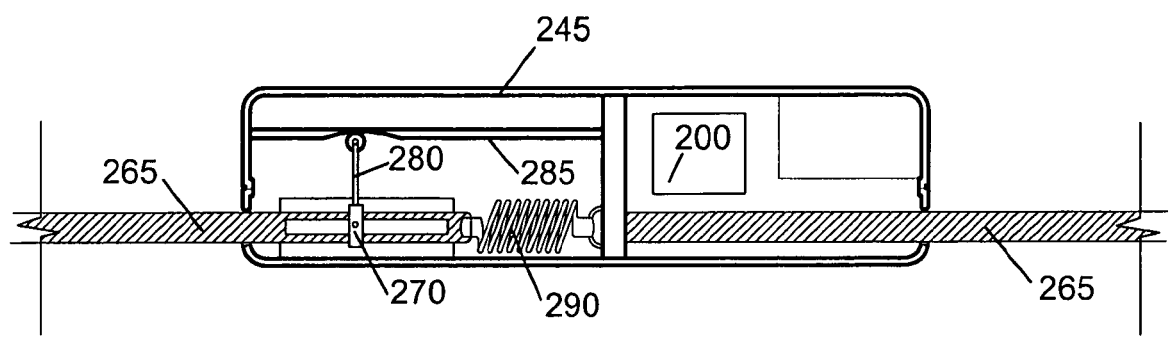
FIG. 2 is a Cross-section view.

FIG. 2 is a cross-section (side view) of the present invention.

It illustrates that belt 265 has one end attached to Housing 245. The other end of belt 265 enters Housing 245 and is attached to Shuttle 270 and too Spring 290. Shuttle 270 travels within Guide 275. Shuttle 270 is attached to Wiper 280. Wiper 280 is an attachment of Membrane Potentiometer 285.

The expansion of the Thorax or Abdomen during inspiration causes Belt 265 to pull on Shuttle 270 moving it from its' rest position. Shuttle 270 moves within Guide 275 and deforms Spring 290. The movement of Shuttle 270 also moves Wiper 280. Wiper 280 is pressed down on the top layer of Membrane Potentiometer 285, which in turn touches the bottom layer of Membrane Potentiometer 285. The touching of the upper and lower layer of Membrane Potentiometer 285 creates a voltage divider circuit. The output is voltage. The voltage is a direct inferential reading of the magnitude of the expansion or contraction of the Thorax/Abdomen at any time. The Computer processes the voltage as a Signal. The Signal output of Membrane Potentiometer 285 varies in direct proportion to the position of Shuttle 270 within Guide 275.

When an exhalation occurs the Thorax or Abdomen contracts, releasing tension on Shuttle 270. Spring 290 moves Shuttle 270 back towards its rest position within Guide 275. Those skilled in the art will understand the method of using Membrane Potentiometers to sense position. The cutaneous rumble effects actuator 200 is attached to the Housing 245.

The collection of elements of FIG. 2 makeup the Integrated Plethysmographic Sensor.

FIG. 3 is a Block Diagram of the manner in which Microphone and Plethysmographic sensor data is converted into Signals.

Referring now to FIG. 3A the Block Diagram is illustrative of the Signal that is outputted from the Integrated Plethysmographic Sensor 301. Buffer 302 conditions the voltage Signal from Plethysmographic Sensor 301. The voltage Signal from Buffer 302 is the Thorax/Abdomen Movement Signal 303. The Computer (not shown in FIG. 3) Processes the Signal 303.

Referring to FIG. 3B the Block Diagram is illustrative of the Process that the Signals of Breathing Sounds 313 and Heart Beat Sound 312 that are extracted. The Microphone 304 detects a multiplicity of Audio Signals. The multiplicity of Audio Signals are comprised of the Audio components of biologic processes (Heart Beats, audio component of the turbulence that occurs in the human respiratory system during respiration, bowels, snoring, wheezing, yawning, coughing, etc) and external interference artifacts. The multiplicity of signals forms a spectrum of Audio frequencies. The elements of the Block Diagram as represented in FIG. 3B (Buffer 305, Bandpass Filter 306, Envelope Detection 307, Log 308, Sum 309, Integrator 310, and Output Scaling 311) act in concert to filter out the extraneous signals so as to export only the Signals of Respiration 313 and the Signals of the Beating Heart 312. The Process is further detailed in the technical paper ENDER, Derek et al. Process for the Detection and Analysis of Respiratory Airflow and Snoring Sounds During Sleep Using Laryngeal Sound Discrimination: Engineering in Medicine and Biology Society, 1992. Vol. 14. Proceedings of the Annual International Conference of the IEEE. Volume 6, Issue, 29 Oct.-1 Nov. 1992 Page(s): 2636-263. Which is hereby incorporated by reference.

The Computer (not shown in FIG. 3) processes the exported Signals. Those skilled in the art will understand this method to extract specific Audio Signals from a multiplicity of Audio Signals.

Referring again to FIG. 3C. The Signals that are derived by the Plethysmographic Sensor 301 and the Microphone 304 are Measured by the Computer (not shown in FIG. 3). Each Signal is Measured for three (3) discrete Parameters. The Measurement quantity is assigned a numeric value that represents a direct inferential reading of the specific Signal Parameter. The Parameters that are Measured are the: Amplitude 313 of the Signal. The Amplitude 313 is representative of the expansion of the Thorax or Abdomen during an inspiration. Duration of the Signal 314. The Duration of the Signal 314 is the amount time that it takes for an discrete inspiration and exhalation to be completed. Periodicity of the Signal 315. The Periodicity of the Signal 315 is the time between discrete exhalations.

Figure 4:
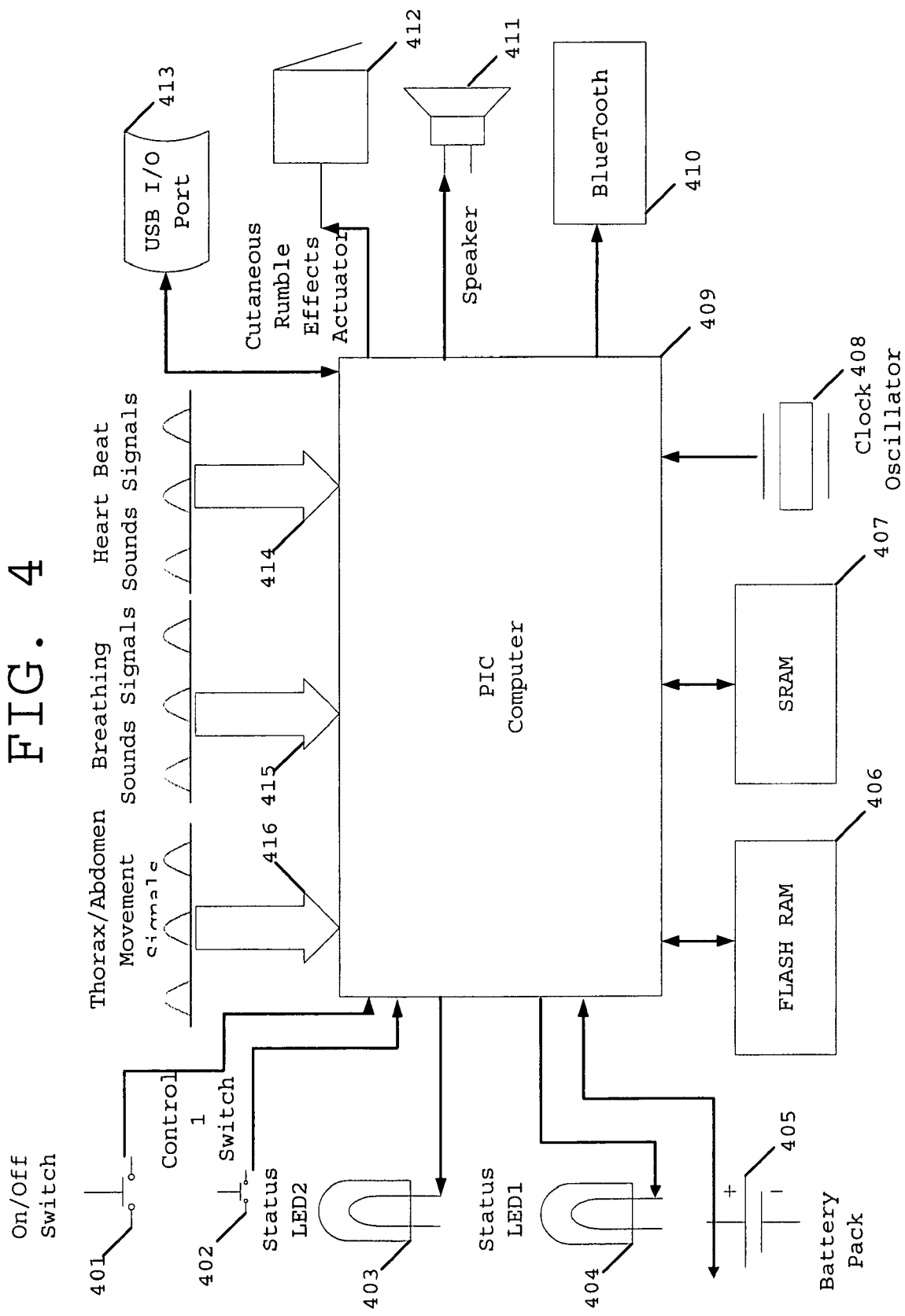
FIG. 4 is a Block diagram of the Electronic and Electrical elements of the invention.

FIG. 4 is a Block diagram of the Electronic and Electrical elements of the invention.

The operation of the invention is illustrated in FIG. 4. It is made up of a number of electronic component sections:

PIC Computer 409 is the Computer of the invention.

On/Off Switch 401 activates and deactivates the invention.

Control1 Switch 402 activation is the method wherein that patient interacts with the invention.

Status LED2 403 is a multicolor LED. The color that it presents to the patient indicates the status of the invention.

Status LED1 404 is a multicolor LED. The color that it presents to the patient indicates the status of the invention. Battery Pack 405 provides electrical power to the invention.

FLASH RAM 406 contains the Force Portraits 601, the Fuzzy Control System Rules, and the Processing program instructions. The Computer 409 and it exchange data over a signal buss. SRAM 407 contains the results of arithmetic computations by the Computer 409. The Computer 409 and it exchange data over a signal buss. Clock Oscillator 408 is the Inventions clock. BlueTooth 410 is the section that receives Audio Portrait Signals, Alarm Signals, and Training Period 1 & 2 spoken commands, converts the signals into Bluetooth formatted Signals and wirelessly transmits the Audio Portrait Signals to a Bluetooth wireless Earbud 715 (not shown if FIG. 4) worn by the patient. Speaker 411 Audio Portrait Signals, Alarm Signals, and Training Period 1 & 2 spoken commands and broadcasts them to the patient.

USB I/O Port 413 is the means by which external devices communicate with the Computer 409. Signals 414, 415, and 416 are the busses by which the Signals are received by the Computer 409 for Processing.

FIG. 5 is a Block Diagram of the Training and Monitoring Processes.

Figures 5A, 5B:
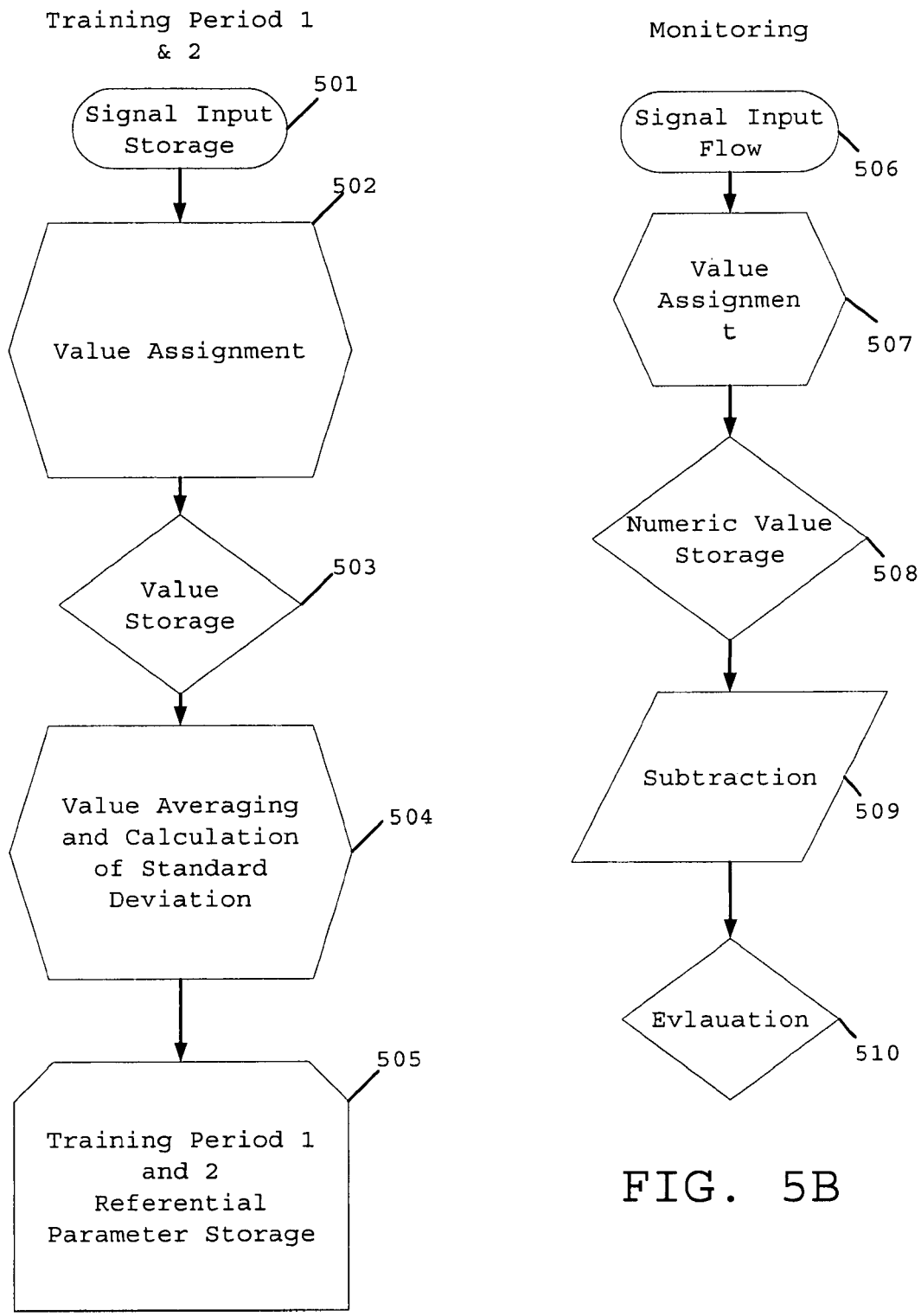
FIGS. 5A, and 5B are Block Diagrams of the Training and Monitoring Processes.

It is a primary object of the present invention to provide a apparatus and method for detecting and terminating an Sleep Apnea event and Hypopnea episode, within seconds of aid detection. To perform the process I draw your attention to FIG. 5A. FIG. 5A is a block diagram of the Process of Training. The Signals that are generated during Training Periods #1 and #2 are used by the invention to perform Self-checking. This Self-checking procedure verifies that the invention is operating as intended.

The Process of Self-Checking commences when the patient dons the invention and presses button On/Off Switch 401 (not shown in FIG. 5). The patient is directed to adjust the Belt 165 (not shown in FIG. 5) and Velcro clasp by plain, spoken commands. These spoken commands are fetched from FLASH RAM 406 (not shown in FIG. 5) by the Computer 409 (not shown in FIG. 5) and broadcast to the patient by Bluetooth wireless 410 (not shown in FIG. 5) to the patients Bluetooth Earbud 715 (not shown in FIG. 5) and/or the Speaker 411 (not shown in FIG. 5). The directions are supplied to the patient to insure that the Integrated Plethysmographics' Shuttle 270 (not shown in FIG. 5) is in its' rest position within Guide 275 (not shown in FIG. 5) that allows for uninterrupted movement of the Shuttle 270 (not shown in FIG. 5) during inspiration and exhalation.

Furthermore, the Signals are Measured to become a set of Referential Parameters (the process that is used to create these Referential Parameters is addressed in detail later in this document).

The Process of Training: During Training Period #1, the patent is directed to breath in specific patterns by plain, spoken commands. These spoken commands are fetched from FLASH RAM 406 (not shown in FIG. 5) by the Computer 409 (not showing FIG. 5) and broadcast to the patient by Bluetooth wireless 410 (not shown in FIG. 5) to the patients Bluetooth Earbud 715 (not shown in FIG. 5) and/or the Speaker 411 (not shown in FIG. 5). This Process of Training commences when the patient dons the invention and presses button On/Off Switch 401 (not shown in FIG. 5) The specific patterns include but not limited to:

"Natural Breathing"
"Deep Breathing"
"Fast Breathing"
"Slow Breathing"
"No Breathing"
"Shallow Breathing"
"Breath while Supine"
"Breath on the patients Left Side"
"Breath on the patients Right Side"
"Breath while Prone"

During Training Period #2 the patent is directed to push the Control1 Switch 402 (not shown in FIG. 5) as they are preparing to go to sleep.

All Signals are Measured by the Computer 409 (not shown in FIG. 5) to derive Values for the Signals intrinsic Parameters. All Signals are Measured and Processed in an identical manner.

To illustrate how Signals are Measured by the Computer 409 (not shown in FIG. 5) to derive Values for the Signals' intrinsic Parameters and then Processed we will use the Measurement of a single Parameter as an example. Review FIG. 5A.

For this example, the Signal Parameter that will be Measured and Processed is "Amplitude" 316 (not shown in FIG. 5): The "Amplitude" is representative of the expansion of the Thorax or Abdomen that occurs during an inspiration:

1. Signal Input Storage 501, collects the stream of Signals 303 (not shown in FIG. 5), 312 (not shown in FIG. 5), and 313 (not shown in FIG. 5) for 60 seconds.

2. Within Block 502 the Signals from within Signal Input Storage 501 are Measured. Values are Processed so that only the largest Value for any Inspiration is kept.
   a. The method of this specific Processing follows this format:
      i. IF Value(Now) is GREATER than or EQUAL to Value(Previous) THEN assign Value(Now) to Value (Previous).
      ii. IF Value(Now) is Less than or Equal to Value (Previous) THEN store Value(Previous) within Value Storage 503 as it is the largest value for this Inspiration.

3. The stored largest Values within Value Storage 503 form a set named VS.

4. The Values set VS is arithmetically Processed in the following manner within Block 504—
   a. Calculate the arithmetic average of the Values in the set VS.
   b. Subtract each Value in the set from the arithmetic average.
   c. Square the deviation of each Value in the set from the arithmetic average.
   d. Calculate the arithmetic average of the Squared deviations.
   e. Calculate the square root of the arithmetic average of the Squared deviations.
   f. The result is the root-mean-square deviation.

5. The arithmetic average of the Values in the set VS is stored as a Referential Parameter in the Training Period 1 and 2 Referential Parameter Storage 505.

6. The root-mean-square deviation of the Values in the set VS is stored as a Referential Parameter in the Training Period 1 and 2 Referential Parameter Storage 505.

The Process of Monitoring: It is a primary object of the present invention to provide an apparatus and method for detecting and terminating a Sleep Apnea event and Hypopnea episode, within seconds of the detection. FIG. 5B is a block diagram of the Process of Monitoring. The Signals Input Flow 506 comprises Signals 303 (not shown in FIG. 5), 312 (not shown in FIG. 5), and 313 (not shown in FIG. 5).

Signals Input Flow 506 is Measured and Processed by the Computer by Value Assignment 507. The Processing steps are:

1. Upon the Measurement by the Computer 409 (not shown in FIG. 5) a Numeric Value is assigned for each Parameter that is Measured.
2. The Numeric Value is stored in Numeric Value Storage 508.
3. Subtraction arithmetic operation 509. Parametric Numeric Value(Now) minus it's arithmetic average Referential Parameter equals Result1.

The Numeric value for a Parameter is further Processed by the Computer (not shown in FIG. 5) by recalling the Referential Parameters specific to the Parameter that is being Processed at this time.

The Processing consists of a series logic operation by the Computer (not shown in FIG. 5). The format of these series of logic operation Performed within Evaluation 510:

1. If Result1 is equal or Greater than 0 then Do Nothing
2. If Result1 is Less than 0 then
   a. Subtract Parametric Numeric Value(Now) from each Value contained within the Value Set of VS.
   b. If any result of the previous operation (step 2a) is a positive integer then:
      I. Divide Result1 by the root-mean square deviation Referential Parameters parameter equals Result2.
      II. If Results2 is Less than 0 then Do Nothing
      III. If Results2 is Greater than 0 then present Results2 to the Fuzzy Control System for determination as to whether Stimulation should be applied.

Figure 6:
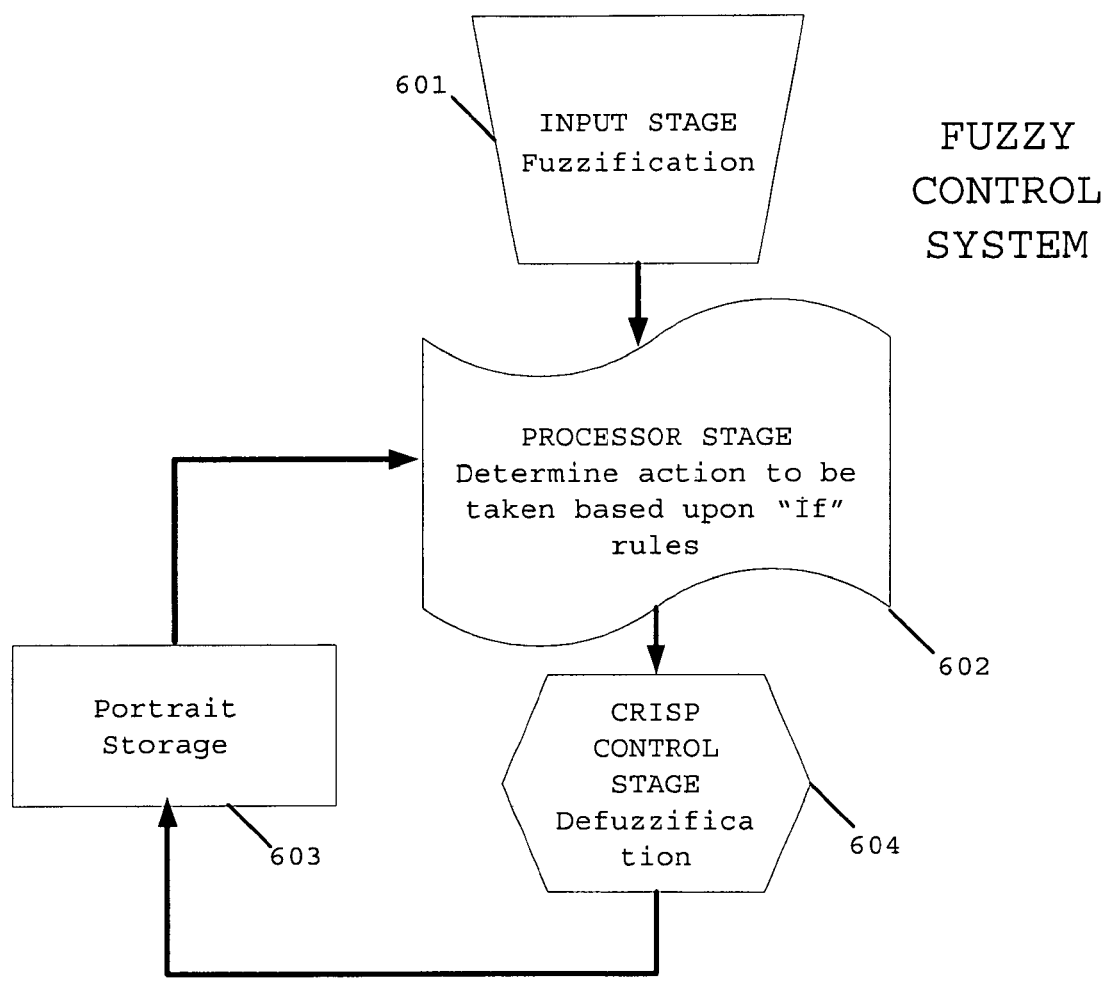
FIG. 6 is a Block Diagram of the Fuzzy Control System.

FIG. 6 is a Block Diagram of the Fuzzy Control System The Detecting and Terminating Process utilizes Fuzzy logic processes. The Fuzzy Control System controls two Processes.

1. Monitoring
2. Stimulation

Fuzzy logic processing is described, for example, in U.S. Pat. No. 7,426,435, issued to GAUTHIER, et al. Sep. 16, 2008, The disclosures of these United States patents are incorporated herein by reference. Another example is NAZERAN, HOMER et al. A Fuzzy Inference System for Detection of Obstructive Sleep Apnea: Proceedings—23rd Annual Conference—IEEE/EMBS Oct. 25-28, 2001, Istanbul, TURKEY, which is hereby incorporated by reference.

Referring to FIG. 6, the Fuzzy Control System Process for Monitoring is as follows:

Result2 values are the input variables to the Fuzzy Control System. The Result2 values are mapped into by sets of membership functions known as "fuzzy sets". The process of converting a Result2 values (in the nomenclature of Fuzzy Logic these Result2 values are referred to as Crisp Input Values) to a fuzzy value is called "fuzzifi-cation". The fuzzification" occurs in the Input stage 601 of the Fuzzy Control System. The "fuzzified" Result2 values are evaluated in the next stage of the Fuzzy Control System, the Processing stage 602. The Processing stage 602 uses a collection of logic rules. The Computer then makes decisions for what action to take based on that collection of logic rules. The Rules are in the form of IF statements:

An example of a logic rule would be:
IF amplitude IS very low AND periodicity IS very long apply stimulation.

In this example, the two input variables are "very low" and "very long" that have values defined as fuzzy sets. The output variable, "stimulation", is also defined by a fuzzy set that can have values like "long", "louder, "less loud", and so on.

The results of the Processing Stage are combined to give a specific ("Crisp") answer; this "Crisp" answer translates results into values. This takes place in the Crisp Control Stage 604. If the "Crisp" answer is to initiate Stimulation then the Process steps are as described or shown herein.

Figure 7:
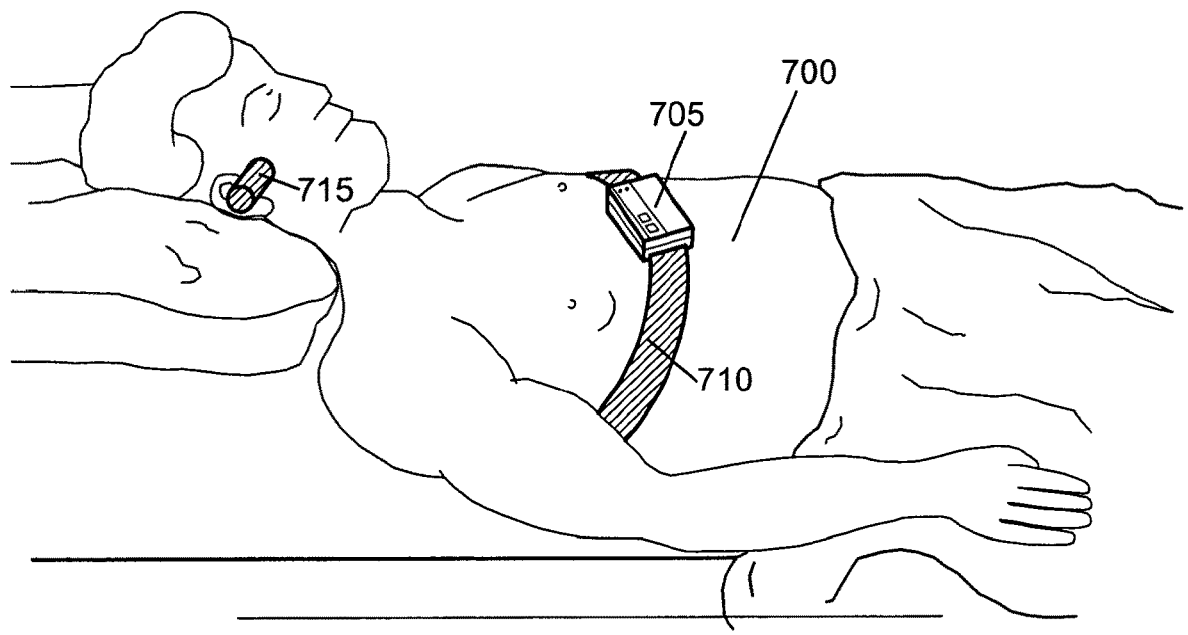
FIG. 7 is a diagram of a Patient wearing the invention.

FIG. 7 is a diagram of a typical Patient wearing the invention. Patient 700, has the positioned the Housing 705 on his Thorax and has fastened Belt 710 to hold it in place. The patient 700 is wearing the Bluetooth Earbud 715.

Figure 8:
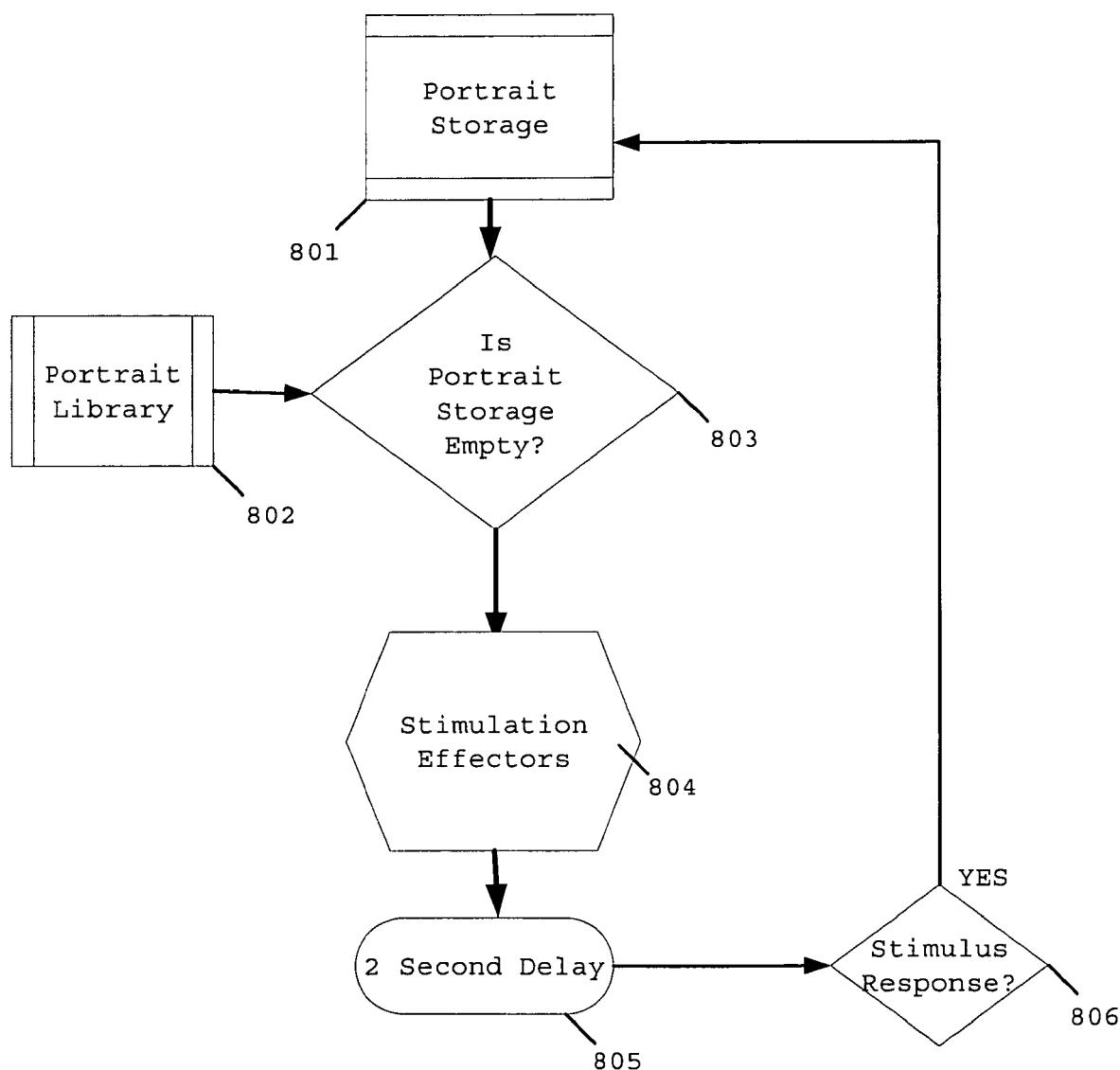
FIG. 8 is a Block Diagram of Portrait Development.

FIG. 8 is a Block Diagram of Portrait Development.

Before continuing it may be advantageous to set forth definitions of certain words and phrases.

Stored Portrait Stimulation Parameters are:
Effective Portraits
Irritation Index
Audio Portrait
Force Portrait
Effectivity Index Effective Portraits:
Is that combination of an Audio Portrait and a Force Portrait that have been found through a Process (described below) to generate an inspiration in a Patient who is having an Sleep Apnea event or Hypopnea episode.

Irritation Index:
The Irritation Index is an arbitrary value assigned to Portraits Audio and Force at the time that the Portrait is created and inputted into the FLASH RAM 406. It is indicative of how reactive a patient would be to that Portrait, As an example, the playing of an Audio file of a woman screaming would be assigned a higher Irritation Index value than that of Audio file of a birds singing.

Force Portrait:
The mechanical tactile sensory stimulator 200 (not shown in FIG. 6) differ from a simple vibrator in that it is capable of simulating a wide range of tactile effects. The Haptic effects are assembled by using software instructions to control the force amplitude, wave shape, and pulse duration to the stimulation effectors. These instructions are combined to form Force Portraits. The Force Portraits are stored in the Haptic effects library area of the Portrait Storage 801 (not shown in FIG. 6). Different Force Portraits are felt as different tactile sensations by the patients. These Force Portraits are assigned an Irritation Index value. The choice of which Force Portrait to use for the mechanical tactile sensory stimulator is determined by the Fuzzy Logic System.

Audio Portrait
A method of Stimulation is the playing of prerecorded Audio files. These Audio files are stored in the Portrait Storage 801 (not shown in FIG. 6) as Audio Portraits. The Audio Portrait is made up the Audio File Name, a Volume value, the File length, and the Audio File Irritation Index value. There are multiplicities of stored Audio Portrait. The Audio files are sent to the patient by a Bluetooth wireless transmitter 410 (not shown in FIG. 6) to a Bluetooth wireless Earbud 715 (not shown in FIG. 6). Bluetooth is a wireless protocol utilizing short-range communications technology facilitating data transmission over short distances from fixed and/or mobile device. Bluetooth wireless communication is described, for example, in U.S. Pat. No. 7,225,064, issued to FUDALI, et al. May 29, 2007. The disclosures of these United States patents are incorporated herein by reference. The choice of which Audio Portrait to use for the Audio Stimulus is determined by the Fuzzy Logic System.

Effectivity Index:
The Effectivity Index is the sum of the Irritation Indexes of an Audio and Force Portraits couple. The larger the numerical value of the Effectivity Index than the more vigorous the Stimulus delivered to the patient. The present invention relates to an apparatus to detect and end an occurrence of a Sleep Apnea event or Hypopnea episode, in a manner that will decrease or eliminate hypoxia, hypercapnia and the disturbance of pulmonary hemodynamics.

To apply Stimulus in a manner that will decrease or eliminate hypoxia, hypercapnia and the disturbance of pulmonary hemodynamics it is necessary to determine what stimuli is both effective in initiating Inspiration within 2 seconds of the stimulus application while simultaneously decreasing or eliminating the disturbance of pulmonary hemodynamics.

The Method to develop a set of stimuli that is both effective in initiating Inspiration within 2 seconds of the Stimulus application while simultaneously decreasing or eliminating the disturbance of pulmonary hemodynamics is as follows. The sets of stimuli are called Effective Portraits.

When the Fuzzy Control System Process of FIG. 6 (not shown in FIG. 8) detects the onset of a Sleep Apnea event or Hypopnea episode, it attempts to select the of Effective Portrait from within Portrait Storage 801.

If there is no Effective Portrait as would happen when the patient initially dons the invention then the Process of developing an Effective Portrait commences:

1. The Fuzzy Control System of FIG. 6 (not shown in FIG. 8) inputs a random selection of a Force and Audio Portrait from the Portrait Library 802 forming a Temporary Couple.

2. The Temporary Couple is sent to the Stimulus Effectors 806.

3. After a 2 Second Delay 805 the Fuzzy Logic System of FIG. 6 (not shown in FIG. 8) Monitors the patient to determine if there is aninspiration.

4. If Fuzzy Logic System of FIG. 6 (not shown in FIG. 8) determines that further Stimulation is required then another random selection of a Force and Audio Portrait is made from the Portrait Library 802 forming another Temporary Couple.

5. This Temporary Couple will have a larger Effectivity Index than the previous Temporary Couple Effectivity Index.

6. This Temporary Couple is sent to the Stimulus Effectors 806.

7. After a 2 Second Delay 805 the Fuzzy Logic System of FIG. 6 (not shown in FIG. 8) Monitors the patient to determine if there is an inspiration.

8. Steps 5-7 cycle until the Fuzzy Logic System of FIG. 6 (not shown in FIG. 8) determines that Stimulus is no longer required. The Temporary Couple is stored in Portrait Storage 801 as an Effective Portrait.

Effectivity of the Effective Portrait changes in a cyclic pattern during sleep as the amount of Stimulus required to initiate an inhalation waxes and wanes.

This is the Method for adapting to that cyclic process—

When the Fuzzy Control System Process of FIG. 6 (not shown in FIG. 8) detects the onset of a Sleep Apnea event or Hypopnea episode, it attempts to use the Effective Portrait that has been stored in Portrait Storage 801.

If there is an Effective Portrait in Portrait Storage 801 then the Fuzzy Control System of FIG. 6 (not shown in FIG. 8) will:

1. Send that Effective Portrait to the Stimulus Effectors 806.

2. After a 2 Second Delay 805 the Fuzzy Logic System of FIG. 6 (not shown in FIG. 8) Monitors the patient. If the Fuzzy Logic System of FIG. 6 (not shown in FIG. 8) determines that further Stimulation is required.

a Force and Audio Portrait is chosen from the Portrait Library 802 forming a Temporary Couple whose Effectivity Index is incrementally greater than the Effectivity Index of the Effective Portrait stored in Portrait Storage 801.

b. Sends that Effective Portrait to the Stimulus Effectors 806.
  i. Step 2 cycles until the Fuzzy Logic System of FIG. 6 (not shown if FIG. 8) determines that there exists' no need further for Stimulation (an inhalation is detected).
  ii. This Temporary Couple replaces the Effective Portrait stored within Portrait Storage 801.

3. If the Fuzzy Logic System of FIG. 6 (not shown in FIG. 8) determines that no further Stimulation is required then when the next Sleep Apnea event or Hypopnea episode is detected.

a Force and Audio Portrait is chosen from the Portrait Library 802 forming a Temporary Couple whose Effectivity Index is incrementally less than the Effectivity Index of the Effective Portrait stored in Portrait Storage 801.

b. Sends that Temporary Couple to the Stimulus Effectors 806.

c. After a 2 Second Delay 805 the Fuzzy Logic System of FIG. 6 (not shown in FIG. 8) Monitors the patient.
  i. If the Fuzzy Logic System of FIG. 6 (not shown in FIG. 8) determines that no further Stimulation is required then this Temporary Couple replaces the Effective Portrait stored within Portrait Storage 801.
  ii. If the Fuzzy Logic System of FIG. 6 (not shown in FIG. 8) determines further Stimulation is required then 1) A Force and Audio Portrait is chosen from the Portrait Library 802 forming a Temporary Couple whose Effectivity Index is incrementally greater than the Effectivity Index of the Effective Portrait stored in Portrait Storage 801.

2) Sends that Effective Portrait to the Stimulus Effectors 806.

3) After a 2 Second Delay 805 the Fuzzy Logic System of FIG. 6 (not shown in FIG. 8) Monitors the patient.

4) Step 3) cycles until the Fuzzy Logic System of FIG. 6 (not shown if FIG. 8) determines that there exists' no need further for Stimulation (an inhalation is detected.

5) This Temporary Couple replaces the Effective Portrait stored within Portrait Storage 801.

CITATION LIST

Patent Literature

U.S. Pat. No. 7,387,608 Apparatus and method for the treatment of sleep related disorders Jun. 1, 2008 Dunlop; David A, Gunderman, Jr.; Robert Dale U.S. Pat. No. 7,371,220 System and method for real-time apnea/hypopnea detection using an implantable medical system May 1, 2008 Koh; Steve, Park; Euljoon, Benser 2005/0085865 Breathing disorder detection and therapy delivery device and method Apr. 1, 2005 Tehrani, Amir J 2006/0097879 SIDS and apnea monitoring system May 1, 2006 Lippincott; Kathy J 2005/0101833 Apparatus for the treatment of sleep apnea May 1, 2005 Hsu, William U.S. Pat. No. 6,935,335 System and method for treating obstructive sleep apnea Aug. 1, 2005 Lehrman; Michael L., Halleck; Michael E U.S. Pat. No. 6,666,830 System and method for detecting the onset of an obstructive sleep apnea event Dec. 1, 2003 Lehrman; Michael L., Halleck; Michael E. Ferguson; Pete, Kumar; Harpal, Lay; Graham, Llewellyn; Mike, Place; John D.

U.S. Pat. No. 6,241,683 Phonospirometry for non-invasive monitoring of respiration Jun. 1, 2001 Macklem; Peter T., Que; Cheng-Li, Kelly; Suzanne M., Kolmaga; Krzystof, Durand; Louis-Gilles U.S. Pat. No. 6,290,654 Obstructive sleep apnea detection apparatus and method using pattern recognition Sep. 1, 2001 Karakasoglu; Ahmet U.S. Pat. No. 6,011,477 Respiration and movement monitoring system Jan. 4, 2000 Teodorescu; Horia-Nicolai, Mlynek; Daniel J.

U.S. Pat. No. 5,853,005 Acoustic monitoring system Dec. 1, 1998 Scanlon; Michael V U.S. Pat. No. 5,769,084 Method and apparatus for diagnosing sleep breathing disorders Jun. 1, 1998 Katz; Richard A., Lawee; Michael S., Newman; A. Kief U.S. Pat. No. 5,555,891 Vibrotactile stimulator system for detecting and interrupting apnea in infants 9/1/1996 Eisenfeld; Leonard I.

U.S. Pat. No. 5,540,733 Method and apparatus for detecting and treating obstructive sleep apnea Jul. 1, 1996 Testerman; Roy L., Erickson; Donald J., Bierbaum; Ralph W.

U.S. Pat. No. 5,522,862 Method and apparatus for treating obstructive sleep apnea Jun. 4, 1996, Testerman; Roy L., Erickson; Donald J.

U.S. Pat. No. 5,277,194 Breathing monitor and stimulator, Jan. 11, 1994. Hosterman; Craig, Smith; Alvin W.

U.S. Pat. No. 5,107,855 Apena monitor for detection of aperiodic sinusoidal movement Apr. 1, 1992 Harrington; Reginald, Crossley; Ralph U.S. Pat. No. 5,050,614 Apparatus and method for inspiration detection Sep. 1, 1991 Logan; Charles H.

U.S. Pat. No. 4,781,201 Cardiovascular artifact filter Nov. 1, 1988 Wright; John C., Triebel U.S. Pat. No. 4,694,839 Auxiliary stimulation apparatus for apnea distress Sep. 1, 1987 Timme; William F.

U.S. Pat. No. 4,686,999 Multi-channel ventilation monitor and method Aug. 1, 1987 Snyder; Leon T., Scarfone; Frank A., Reuss; James L., Campen; George V., Yates; George H.

U.S. Pat. No. 4,365,636 Method of monitoring patient respiration and predicting apnea there from Dec. 1, 1982 Barker; Kent R.

U.S. Pat. No. 4,296,757 Respiratory monitor and excessive intrathoracic or abdominal pressure indicator Oct. 1, 1981 Taylor; Thomas CONTINUATION APPLICATION 2505240 OSA HYPDXIA ONSET DETECTOR AND INTERRUPTOR Nov. 26, 2007

Non-Patent Literature

H. SCHNEIDER et al, "Effects of arousal and sleep state on systemic and pulmonary hemodynamics in obstructive apnea", J. Appl. Physiol. 88: 1084-1092, 2000.

D. M. Carlson et al, "Acoustically induced cortical arousal increases phasic pharyngeal muscle and diaphragmatic EMG in NREM sleep", Journal of Applied Physiology, Vol 76, Issue 4 1553-1559.

W. T. McNicholas, "Arousal in the sleep apnea syndrome: a mixed blessing?", Eur Respir J 1998; 12: 1239-1241.

Robert C. Basner M D et al, "Respiratory and Arousal Responses to Acoustic Stimulation", Chest. 1997; 112: 1567-1571.

Gang Bao et al., "Acute and chronic blood pressure response to recurrent acoustic arousal in rats", Am J Hypertens (1999) 12, 504-510.

R. C. Basner et al, "Effect of induced transient arousal on obstructive apnea duration", J. App Physiol. 78(4): 1469-1476, 1995.

Dina Brooks et al, "Obstructive Sleep Apnea as a Cause of Systemic Hypertension Evidence from a Canine Model", J. Clin. Invest. Volume 99, Number 1, January 1997, 106-109.

MARY J. MORRELL et al, "Sleep Fragmentation, Awake Blood Pressure, and Sleep-Disordered Breathing in a Population-based Study", Am. J. Respir. Crit. Care Med., Volume 162, Number 6, December 2000, 2091-2096.

Robert C. Basner et al, "Respiratory and Arousal Responses to Acoustic Stimulation", Chest 1997; 112; 1567-1571.

RICHARD S. T. LEUNG et al, "Sleep Apnea and Cardiovascular Disease", Am. J. Respir. Crit. Care Med., Volume 164, Number 12, December 2001, 2147-2165.

Denise M. O'Driscoll et al, "Cardiovascular response to arousal from sleep under controlled conditions of central and peripheral chemoreceptor stimulation in humans", J Appl Physiol 96:865-870, 2004.

Denise M. O'Driscoll et al, "Occlusion of the upper airway does not augment the cardiovascular response to arousal from sleep in humans", J Appl Physiol 98:1349-1355, 2005.

U. Leuenberger et al, "Surges of muscle sympathetic nerve activity during obstructive apnea are linked to hypoxemia", Am. J. Respir. Crit. Care Med., Volume 164, Number 12, December 2001, 2147-2165.

RICHARD S. T. LEUNG et al, "Sleep Apnea and Cardiovascular Disease", Journal of Applied Physiology, Vol 79, Issue 2 581-588.

Richard B. Berry M D, "Sleep Apnea Impairs the Arousal Response to Airway Occlusion", Chest. 1996; 109:1490-1496.

T. KATO et al, "Experimentally induced arousals during sleep: a cross-modality matching paradigm", J. Sleep Res. (2004) 13, 229-23.

Christian Guilleminault et al, "The effect of CNS activation versus EEG arousal during sleep on heart rate response and daytime tests", Clinical Neurophysiology 117 (2006) 731-739.

Emilia Sforza, M D et al, "Effects of Sleep Deprivation on Spontaneous Arousals in Humans", SLEEP, Vol. 27, No. 6, 2004.

J. F. Masa et al, "Assessment of thoracoabdominal bands to detect respiratory effort-related arousal", Eur Respir J 2003; 22: 661-667.

R. C. Basner et al, "Effect of induced transient arousal on obstructive apnea duration", J Appl Physiol 78: 1469-1476, 1995.

HIROSHI MIKI et al, "New Treatment for Obstructive Apnea Syndrome by Electrical Stimulation of Submental Region", Tohoku J. exp. Med., 1988, 154, 91-92.

C. Guilleminault et al, "The effect of CNS activation versus EEG arousal during sleep on heart rate response and daytime tests", Clinical Neurophysiology, Volume 117, Issue 4, Pages 731-739.

Immersion Corporation, "Next-generation TouchSense Vibration for Video Game Console Systems", 31 Aug. 2006.

Sheroz Khan, I Adam et al, "Rule-Based Fuzzy Logic Controller with Adaptable Reference", International Journal of Intelligent Technology Volume 3 Number 1.

E. Sforza et al, "Nocturnal evolution of respiratory effort in obstructive sleep apnoea syndrome: influence on arousal threshold, Eur Respir J 1998; 121257-126 DOI: 10.1183/09031936.98.12061257.

Homer Nazeran et al, "A Fuzzy Inference System for Detection of Obstructive Sleep Apnea". Proceedings—23rd Annual Conference—IEEE/EMBS Oct. 25-28, 2001, Istanbul, TURKEY.

What is claimed:

1. A system for treating a breathing disorder comprising:
a sensor capable of detecting physiologic signals;
a patient stimulator configured to operate independently of any administration of gases or positive airway pressure;
a processor connected to the sensor and the patient stimulator, the processor being configured to perform the following operations without entry of baseline parameters and without the intervention of health professionals to evaluate results from a polysomnogram or to determine parameters of the system:
self-determine baseline parameters;
process information from the sensor to detect patterns and abnormalities of respiration of a patient, and to determine a physiologic state of the patient;
select, in response to the physiologic state of the patient, from a group of stimuli consisting of stationary auditory stimuli and non-stationary auditory stimuli having time-varying frequency content, a first stimulus comprising a stationary auditory stimulus and a second stimulus comprising a non-stationary auditory stimulus having time-varying frequency content;
configure, in response to the physiologic state of the patient, attributes of each selected stimulus to elicit a desired physiologic response comprising initiation of inhalation while avoiding or mitigating an undesired physiologic response comprising recruitment of the ascending arousal system and transition from a deeper stage of sleep to a lighter stage of sleep, the attributes including a start timing, an intensity, and a duration; and
generate a control signal to cause the stimulator to deliver each selected stimulus in response to detecting a physiologic state that predicts an onset of an apnea or a hypopnea, and to terminate delivery of stimuli immediately upon detection of an inhalation, so that stimuli are not delivered when the patient is breathing normally.

2. The system of claim 1, the processor being further configured to generate a control signal to cause the stimulator to deliver each selected stimulus at a start time synchronized to a physiologic signal detected by the sensor.

3. The system of claim 1, wherein the processor is further configured to generate a control signal to cause the stimulator to deliver each selected stimulus to elicit initiation of inhalation before airflow has been interrupted for a full 10 seconds, so that the interruption of airflow is less than 10 seconds.

4. The system of claim 1, wherein the processor is further configured to configure the modifiable attributes and timing of each selected stimulus to prevent habituation.

5. The system of claim 1, wherein the processor is further configured to configure the attributes of each selected stimulus to avoid or mitigate an additional undesired physiologic response selected from the group consisting of altered cardiac activity, increased systolic blood pressure, and increased circulating catecholamines.

6. The system of claim 1, wherein the sensor comprises a microphone.

7. The system of claim 1, wherein the sensor comprises a plethysmograph.

8. The system of claim 1, wherein the sensor comprises a variable resistance sensor.

9. The system of claim 1, wherein the sensor comprises a variable voltage sensor.

10. The system of claim 1, wherein the sensor comprises a strain gauge.

11. The system of claim 1, wherein the sensor comprises an accelerometer.

12. The system of claim 1, wherein the sensor comprises a Hall Effect transducer.

13. The system of claim 1, wherein the sensor comprises an ultrasonic sensor.

14. The system of claim 1, wherein the sensor comprises a photodetector.

15. The system of claim 1, wherein the non-stationary auditory stimuli having time-varying frequency content comprise naturalistic audio signals, naturalistic audio signals being signals having logarithmically distributed spectrotemporal modulations.

16. The system of claim 1 wherein the processor is further configured to select, in response to the physiologic state of the patient, an additional stimulus from a group of stimuli consisting of haptic stimuli.

17. The system of claim 1 wherein the processor is further configured to select, in response to the physiologic state of the patient, an additional stimulus from a group of stimuli consisting of optical stimuli.

18. A method for treating a breathing disorder comprising:
operating without entry of baseline parameters;
operating without the intervention of health professionals to evaluate results from a polysomnogram or to determine configuration parameters;
self-determining baseline parameters;
processing information from a sensor capable of detecting physiologic signals to detect patterns and abnormalities of respiration of a patient, and to determine a physiologic state of the patient;
selecting, in response to the physiologic state of the patient, from a group of stimuli consisting of stationary auditory stimuli and non-stationary auditory stimuli having time-varying frequency content, a first stimulus comprising a stationary auditory stimulus and a second stimulus comprising a non-stationary auditory stimulus having time-varying frequency content;
configuring, in response to the physiologic state of the patient, attributes of each selected stimulus to elicit a desired physiologic response comprising initiation of inhalation while avoiding or mitigating an undesired physiologic response comprising recruitment of the ascending arousal system and transition from a deeper stage of sleep to a lighter stage of sleep, the attributes including a start timing, an intensity, and a duration; and
delivering, independent of any administration of gases or positive airway pressure, each selected stimulus to the patient using the patient stimulator in response to detecting a physiologic state that predicts an onset of an apnea or a hypopnea, and terminating delivery of stimuli immediately upon detection of inhalation, so that stimuli are not delivered when the patient is breathing normally.

19. The method of claim 18, wherein each selected stimulus is delivered at a time synchronized to a physiologic signal detected by the sensor.

20. The method of claim 18, wherein a physiologic state is detected that predicts onset of an apnea or hypopnea and each selected stimulus is delivered to elicit initiation of inhalation before airflow has been interrupted for a full 10 seconds, so that the interruption of airflow is less than 10 seconds.

21. The method of claim 18, wherein the attributes and timing of each selected stimulus are chosen to prevent habituation.

22. The method of claim 18, wherein the steps of the method are performed while the patient is using a Positive Airway Pressure machine.

23. The method of claim 18, wherein the attributes of each selected stimulus are further configured to avoid an additional undesired physiologic response selected from the group consisting of altered cardiac activity, increased systolic blood pressure, and increased circulating catecholamines.

24. The method of claim 18, wherein the sensor comprises a microphone.

25. The method of claim 18, wherein the sensor comprises a plethysmograph.

26. The method of claim 18, wherein the sensor comprises a variable resistance sensor.

27. The method of claim 18, wherein the sensor comprises a variable voltage sensor.

28. The method of claim 18, wherein the sensor comprises a strain gauge.

29. The method of claim 18, wherein the sensor comprises an accelerometer.

30. The method of claim 18, wherein the sensor comprises a Hall Effect transducer.

31. The method of claim 18, wherein the sensor comprises an ultrasonic sensor.

32. The method of claim 18, wherein the sensor comprises a photodetector.

33. The method of claim 18, wherein an additional stimulus is selected, in response to the physiologic state of the patient, from a group of stimuli consisting of haptic stimuli.

34. The method of claim 18, wherein an additional stimulus is selected, in response to the physiologic state of the patient, from a group of stimuli consisting of optical stimuli.

* * * * *